US010502698B2

(12) United States Patent
Yamakawa et al.

(10) Patent No.: US 10,502,698 B2
(45) Date of Patent: Dec. 10, 2019

(54) DATA PROCESSING APPARATUS AND DATA PROCESSING METHOD FOR X-RAY EXAMINATION, AND X-RAY EXAMINATION SYSTEM PROVIDED WITH THE DATA PROCESSING APPARATUS

(71) Applicant: JOB CORPORATION, Kanagawa (JP)

(72) Inventors: Tsutomu Yamakawa, Kanagawa (JP); Shuichiro Yamamoto, Kanagawa (JP); Yoshiharu Obata, Kanagawa (JP); Masashi Yamasaki, Kanagawa (JP); Masahiro Okada, Kanagawa (JP)

(73) Assignee: JOB CORPORATION, Kanagawa (JP)

( * ) Notice: Subject to any disclaimer, the term of this patent is extended or adjusted under 35 U.S.C. 154(b) by 0 days.

(21) Appl. No.: 15/329,598

(22) PCT Filed: Apr. 20, 2016

(86) PCT No.: PCT/JP2016/062550
§ 371 (c)(1),
(2) Date: Jan. 27, 2017

(87) PCT Pub. No.: WO2016/171186
PCT Pub. Date: Oct. 27, 2016

(65) Prior Publication Data
US 2018/0209922 A1 Jul. 26, 2018

(30) Foreign Application Priority Data
Apr. 20, 2015 (JP) ................. 2015-085551

(51) Int. Cl.
A61B 6/00 (2006.01)
G01N 23/04 (2018.01)
(Continued)

(52) U.S. Cl.
CPC ............. G01N 23/04 (2013.01); A61B 6/00 (2013.01); A61B 6/12 (2013.01); A61B 6/14 (2013.01);
(Continued)

(58) Field of Classification Search
CPC ...... G01N 23/04; G01N 23/083; G01N 23/18; G01N 2223/401; G01N 2223/402;
(Continued)

(56) References Cited

U.S. PATENT DOCUMENTS

2007/0030944 A1  2/2007  Grasruck et al.
2007/0092127 A1  4/2007  Grasruck et al.
2010/0226474 A1  9/2010  Yamakawa et al.

FOREIGN PATENT DOCUMENTS

JP  2007-136163  6/2007
JP  2010-091483  4/2010
(Continued)

OTHER PUBLICATIONS

Watabiki et al., "Development of Dual-Energy X-ray Inspection System", Anritsu Technical No. 87, Mar. 2012.

Primary Examiner — Jurie Yun
(74) Attorney, Agent, or Firm — Clark & Brody

(57) ABSTRACT

The type and/or properties of a substance included in an object is identified highly accurately regardless of the thickness of the substance. A data processing apparatus processes counts detected at each of pixels of a photo counting detector in each of a plurality of energy ranges of X-rays. The X-rays are radiated from an X-ray tube, and transmitted through an object. The apparatus calculates an image of the object based on the counts, and sets a region of interest on the image. The apparatus further removes, from the image, pixel information showing a background present in the region of interest, and calculates, pixel by pixel, inherent information inherent to the substance, based on the counts detected at each of the respective pixels in each of the energy ranges of the X-rays in the region of interest. The inherent information indicates a transmission characteristic inherent to the X-rays.

19 Claims, 18 Drawing Sheets

(51) Int. Cl.
  *A61B 6/12* (2006.01)
  *A61B 6/14* (2006.01)
  *G01N 23/18* (2018.01)
  *G01N 23/087* (2018.01)
  *G01N 23/083* (2018.01)
  *G06T 7/00* (2017.01)
  *G06T 11/20* (2006.01)

(52) U.S. Cl.
  CPC ......... *G01N 23/083* (2013.01); *G01N 23/087* (2013.01); *G01N 23/18* (2013.01); *G06T 7/0004* (2013.01); *G06T 7/0012* (2013.01); *G06T 11/206* (2013.01); *G01N 2223/401* (2013.01); *G01N 2223/402* (2013.01); *G06T 2207/10116* (2013.01); *G06T 2207/30068* (2013.01); *G06T 2207/30128* (2013.01)

(58) Field of Classification Search
  CPC ......... A61B 6/14; A61B 6/4241; A61B 6/482; A61B 6/5252; G06T 7/00; G06T 7/0012; G06T 7/0004; G06T 11/20; G06T 11/206; G06T 2207/30128; G06T 2207/10116; G06T 2207/30068; G06T 2207/30004; G06T 2207/30108; G06T 2207/30112
  USPC ...... 378/62, 98.8, 98.9, 98.11; 382/128, 132
  See application file for complete search history.

(56) References Cited

FOREIGN PATENT DOCUMENTS

| | | |
|---|---|---|
| JP | 2013-119000 | 6/2013 |
| WO | 2007/110465 | 10/2007 |
| WO | 2013/047778 | 4/2013 |
| WO | 2014/126189 | 8/2014 |
| WO | 2014/181889 | 11/2014 |
| WO | 2015/111728 | 7/2015 |

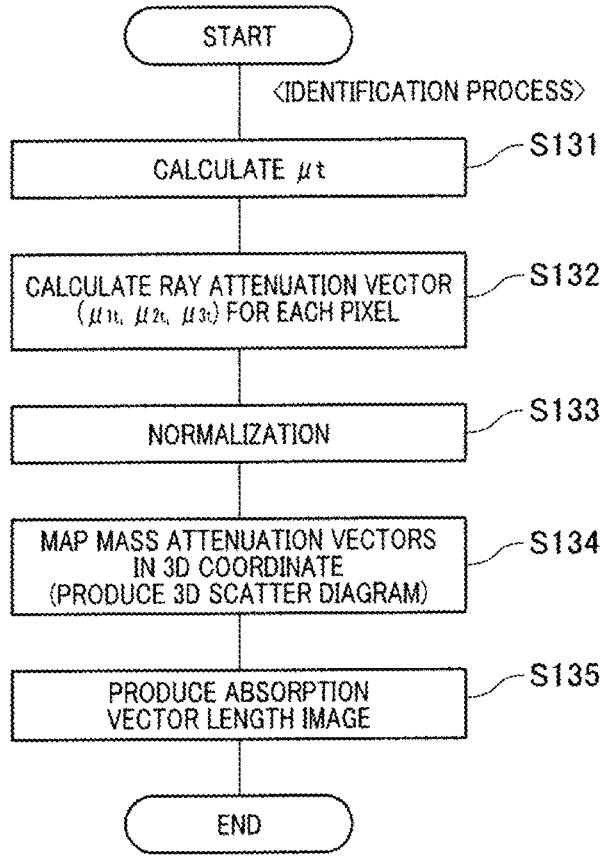
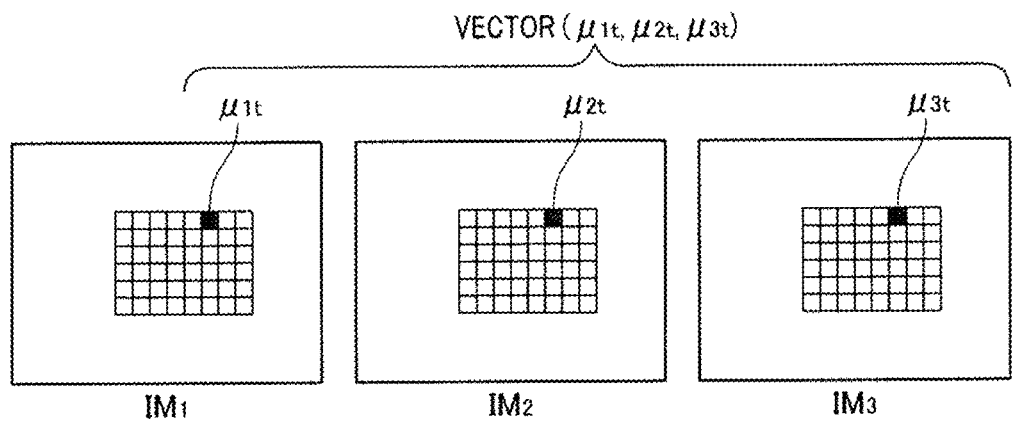

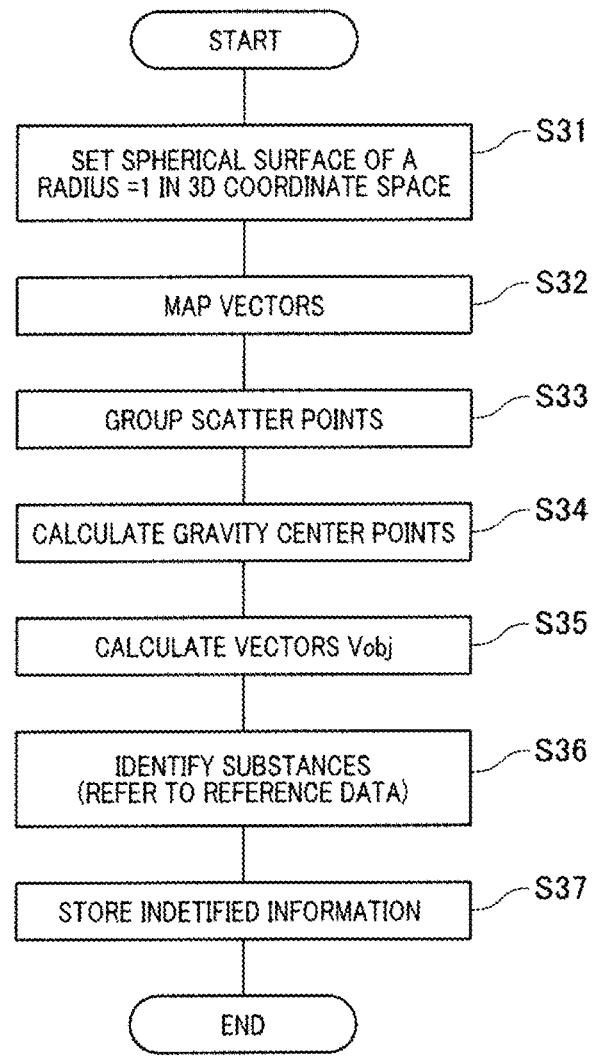

- S15-1: GROUPING (DENSITY AND/OR COLORS)
- S15-2: 3D DISPLAY

- S15-11: DESIGNATE VIEWING DIRECTION
- S15-12: RE-CALCULATION
- S15-13: RE-DISPLAY

- S15-21: READ DATA OF 3D SCATTER POINTS
- S15-22: PROJECT THE READ DATA TO 2D SURFACE
- S15-23: 2D DISPLAY

DATA PROCESSING APPARATUS AND DATA PROCESSING METHOD FOR X-RAY EXAMINATION, AND X-RAY EXAMINATION SYSTEM PROVIDED WITH THE DATA PROCESSING APPARATUS

TECHNICAL FIELD

The present invention relates to a data processing apparatus and a data processing method which process X-ray transmission data acquired by scanning an object with X-rays, and an X-ray examination system equipped with such a data processing apparatus. In particular, the present invention relates to a data processing apparatus, a data processing method and an X-ray examination system, which has a function of i) detecting at least the type or properties of a region of interest of an object being examined, such as food items, industrial products, a part of the human body, or a substance differing from the components of the object, the substance possibly being present in or on the object, or ii) identifying (determining or estimating) from X-ray transmission data the type or properties of the object or the substance.

RELATED ART

In recent years, the need for identifying the type and/or properties of an object by using X-rays has arisen in various places. An example can be seen in inspecting foreign materials which possibly be contained in various food items, which has shown a great rise in view of maintaining public health and food safety.

For such a need, various kinds of X-ray inspection have been proposed. Among them, the most spotlighted inspection method is a method with which X-rays are radiated toward food so as to transmit therethrough so that data of transmitted X-rays are processed to acquire information on substances in or on the food. An example can be provided as an in-line X-ray inspection system in which an X-ray source and a detector are arranged with a conveyance belt located therebetween, and food being inspected is placed on the belt. In this system, the food on the belt (line) is conveyed and passes an X-ray radiation field produced between the X-ray source and the detector. X-rays which have passed through the food are detected by the detector located under the belt, and processed into detection data from which images are generated. The images are then subjected to, for example, designated software processing so that foreign matter which have possibly been contained in the food can be detected based on shadows of the images. In this case, objects being inspected are not necessarily limited to foreign matter, but may be substances which will cause contrast differences for the X-rays and whose sizes, shapes, and/or weights should be obtained more accurately.

In such an X-ray inspection, it has been desired to widen its applications more than now. For example, there is a need for security check in facilities such as at airports, in which, without opening bags or mail articles, types and/or positions of unknown contents in such bags etc. are desired to be detected. In addition, the foregoing foreign matter inspection can be used in a case where foreign matter (e.g., a metal piece) possibly be contained in a previously known object (e.g., food item such as bread). In this case, there is also a need for detecting whether or not the foreign matter is present therein and, if there is the foreign matter, deciding the actual type of the matter. In other words, there has been a higher potential need for identifying, using the X-rays, the type and/or three-dimensional position of the object (substance).

For responding to this growing need, there is known a technique explained in PTL 1: JP-A 2010-091483, for example. This PTL 1 provides a method and a system for detecting foreign matter, which is based on an examination technique referred to as a dual energy method (or a subtraction method). This examination method utilizes a difference in X-ray transmission information, which is caused when two types of energies (wavelengths) of X-rays pass through a substance. Practically, two types of X-rays having lower and higher energies are used to produce X-ray images from those X-rays, and the produced images are subjected to mutual subtraction, so that an image having pixel components showing a contaminating foreign matter can be extracted. This difference image is then subjected to comparison with a threshold, whereby the foreign matter is detected. This is a basic scheme of this examination. Especially, in the method disclosed by PTL 1, suitable parameters are automatically set for the difference computation, which is led to higher-sensitivity foreign matter detection.

The foregoing PTL 1 additionally shows that it is possible to use an X-ray detector capable of detecting incidence of X-ray photons using a system in which the energies of the X-ray photons are discriminated in amounts thereof. That is, as means for concurrently obtaining two types of X-rays having lower and higher energies, it is also suggested to use a known photon counting X-ray emission and detection system.

Meanwhile, as the examination method based on the dual energy method, there is also known a technique disclosed by non-PTL 1. This non-PTL 1 provides a system employing the foregoing basic structure for the dual energy method, and in addition to this, an improvement for objects overlapped on one another on the belt. Even if such overlapped objects are present on the belt, the system is devised to prevent such overlapped objects from being detected as foreign matter, thereby enabling the system to detect the foreign matter with higher sensitivities.

CITATION LIST

Patent Literature

[PTL 1] JP-A 2010-091483
[PTL 2] JP-A 2013-119000

Non Patent Literature

[Non-PTL 1] Anritsu Technical No.87, March 2012, "Development of Dual-Energy X-Ray Inspection System"

Technical Problem

It is possible to raise detection sensitivity of an object or foreign matter which possibly be contained in the object using the dual-energy method set forth in the foregoing PTL 1 or non-PTL 1. However, it is very difficult to obtain information showing what kind of foreign matter is contaminating an object or, in addition to this, where the foreign matter is located three-dimensionally in the object, which are of great interest in foreign matter inspection.

That is, the difficulty of identifying (determining or estimating) the types or other information of foreign matter results in difficulty of identifying the type of substance itself through which the X-rays pass or, in addition to this, the three-dimensional position of the substance. This is very inconvenient in cases where, for example, foreign matter is desired to be inspected as to whether or not the foreign matter is truly contaminating an object whose type itself is unknown.

In order to remove such a drawback, the method disclosed by PTL 2 is proposed. This proposal uses images acquired from a tomographic apparatus or other apparatus which operates using a laminography technique to identify types of substances contained in an object with precision in a convenient manner. Specifically the energy of X-rays is divided into a plurality of energy ranges, in each of which the X-ray photons are counted and the counts are processed into reconstructed object images. These images are used to identify a substance which is present in a region of interest of the object. If using this method, a reference image is produced based on the counts obtained by imaging a substance whose thickness and density are uniform, and the pixel values of the object image are normalized, pixel by pixel, by the pixel values of the object image by the pixel values of the reference image. From the normalized pixel values of the object image, a two-dimensional scatter diagram is produced which has two axes; one axis is assigned to X-ray absorption information and the axis is assigned to X-ray beam hardening information. This scatter diagram is used to provide identification information which indicates the types of substances which are present in an imaged portion of an object.

However, the substance identifying technique set forth in PTL 2 is premised on obtaining a scatter diagram. Using the scatter diagram is good for visually understanding how substances are mixed in an object. In this disclosed technique, however, count information in X-ray energy ranges is subjected to division using an original image in order to calculate values on the beam-hardening axis of the diagram. Hence, there are various inevitable drawbacks, which are such that noise increase in images, larger errors of approximation tend to occur due to insufficient control of passing points (i.e., points chosen on various conditions including a pass through a coordinate origin) of an approximation curve (calculated on a least square approach), stable results are unobtainable, not all the acquired data are used in producing a scatter diagram, and others.

On the other hand, if adopting the conventional inspection method set forth in foregoing patent literature, there is another difficulty in obtaining both a sufficient theoretical base and a higher detection precision, which are for knowing properties of substances. This means that it is possible to raise detection sensitivity if a particular object and a particular imaging condition are set, but such imaging is limited to a narrower range of applications, thus being short of versatility in the inspection.

SUMMARY

In view of the foregoing situations of the conventional X-ray inspection (examination), it is thus desired to provide i) a data processing apparatus and a data processing method, which are able to identify (estimate or determine) the type or properties of a substance composing an object being inspected or examined by X-rays or a part (an interested portion) of the object, regardless of the thickness of the object or the part thereof, and ii) an X-ray examination system equipped with such a data processing apparatus or capable of executing such a data processing method.

Solution to Problem

In order to accomplish the foregoing object, there is provided a data processing apparatus according to exemplary embodiments. This apparatus processes counts obtained every pixel in each of a plurality of X-ray energy ranges, where the X-rays are emitted by an X-ray tube and transmitted through an object, and the counts are detected by a photon counting detector receiving the transmitted X-rays. The data processing apparatus includes image calculating means calculating an image of the object based on the counts, region-of-interest setting means setting a region of interest on the image, background removing means removing, from the image, pixel information which composes a background of a substance present in the region of the interest, and inherent information calculating means calculating, as inherent information, pixel by pixel, inherent transmission properties of the substance to the X-rays, based on the counts Preferably, the inherent information can be set as being at least one of I) information indicating a scatter diagram showing both i) directions provided when the transmission characteristics of each of the pixels are vector amounts (where the vectors are obtained in each of the X-ray energy ranges for example) and ii), in a pseudo manner (virtually), an energy spectrum of the X-rays which have passed the substance; or II) attenuation information showing, in a pseudo manner (or virtually), i) the lengths of the vectors and ii) a degree of attenuation of the X-rays caused during passing the object.

Another mode of the exemplary embodiments is provided as a method of processing counts obtained for every pixel in each of a plurality of X-ray energy ranges, where the X-rays are emitted by an X-ray tube and transmitted through an object, and the counts are detected by a photon counting detector receiving the transmitted X-rays. With this method, an image of the object is calculated based on the counts, a region of interest is set on the image, the background (pixel information) of the substance, which is present in the region of interest, is removed from the image, and inherent transmission characteristics of the substance to the X-rays is calculated, as inherent information based on the counts obtained every pixel in each of the X-ray energy ranges in the region of interest.

Another mode of the exemplary embodiments relates to an X-ray examination system provided with the foregoing data processing apparatus.

Main technical terms used in the exemplary embodiments are defined as follows.

First of all, the term "X-ray examination system" includes a medical X-ray radiographing apparatus and a medical X-ray diagnostic apparatus and also includes an X-ray nondestructive inspection apparatus. The term "X-ray inspection" also conceptually includes medical X-ray examination and nondestructive inspection.

In addition, the term "object being examined" is defined as an object placed in the object space of an X-ray examination system, in which the object undergoes scanning by X-rays for acquiring frame data as X-ray transmission data.

The term "the whole of an object being examined" means the whole of substances composing each object. For example, when the object being examined is food (for instance, vegetables such as peppers or tomatoes, sandwich loaves, pot noodles, edible meats, or fish), the whole of the object means individual items placed on the conveyance belt of the X-ray examination system for inspection. When the object is composed of industrial products or pieces of baggage inspected in an airport, the whole of each object means each item subjected, as an separate thing, to inspection performed by the X-ray examination system.

In contrast, the term "part of an object being examined" is defined as a term which shows only a part of goods being examined. This part is, for example, designated automatically or by hand in an X-ray perspective image, for example. By way of example, in inspecting foreign matter in vegetables, the part of such an object is referred to as a part of each of many vegetables (e.g., cucumbers or tomatoes) carried by the conveyance belt of an X-ray examination system. In cases where a region of interest (i.e., a part of an object) designated in an X-ray perspective image of the object is different from the original composition of the object, it can be evaluated such that foreign matter is contaminating the part designated using the region of interest.

Incidentally, in this foreign matter inspection, the remaining parts other than the foreign matter are processed as background components in data processing. Hence, the background components are data derived from compositions (containing air) of the object itself, which are present in both the background region and the peripheries thereof. When the whole of an object is designated as a target region for identifying substances or determining properties, the background components are only know components including air and the conveyance belt for the inspection.

In addition, the "identification" of a substance is to perform discrimination to know what type of material that the substance is made, so that this term, identification, can be replaced by "determination or estimation" in this application. The "properties" of a substance is to perform discrimination to know what physical state that compositions of the substance are, and, if an edible meat block is picked up as an easily understandable example as an object being examined, this term, properties, is referred to as a ratio between muscle and fat contained in the edible meat block.

Further, "a substance present in a region of interest" i) may be the whole or a part of an object being examined, or ii) may be present in the region of interest but a substance (such as a substance of interest including foreign matter) which is different from the object itself.

Effects

In this way, the substance identification includes various types of modes, which are to identify the type of an object itself, to identify properties of an object itself, to detect that there is a substance other than the compositions of an object itself, and to identify the type of a substance other than the components of an object itself.

BRIEF DESCRIPTION OF DRAWINGS

In the accompanying drawings:
FIG. 7 is an outlined flowchart explaining a key part of the substance identification performed by the data processor in the present embodiment;
FIG. 8 is an illustration explaining generation of a three-dimensional vector showing an X-ray absorption amount, from each of the respective pixels composing a region of interest in an image obtained in an energy range;
FIG. 9 is an outlined flowchart explaining a process performed in stages from generation of a three-dimensional scatter diagram to presentation of identified information.

DESCRIPTION OF EMBODIMENTS

Hereinafter, reference to accompanying drawings, an embodiment of a data processing apparatus and a data processing method, which are for X-ray examination, will now be described, and embodiments of X-ray examination systems provided with the data processing apparatus will then be described as modifications.

[First embodiment]

Figure 1:
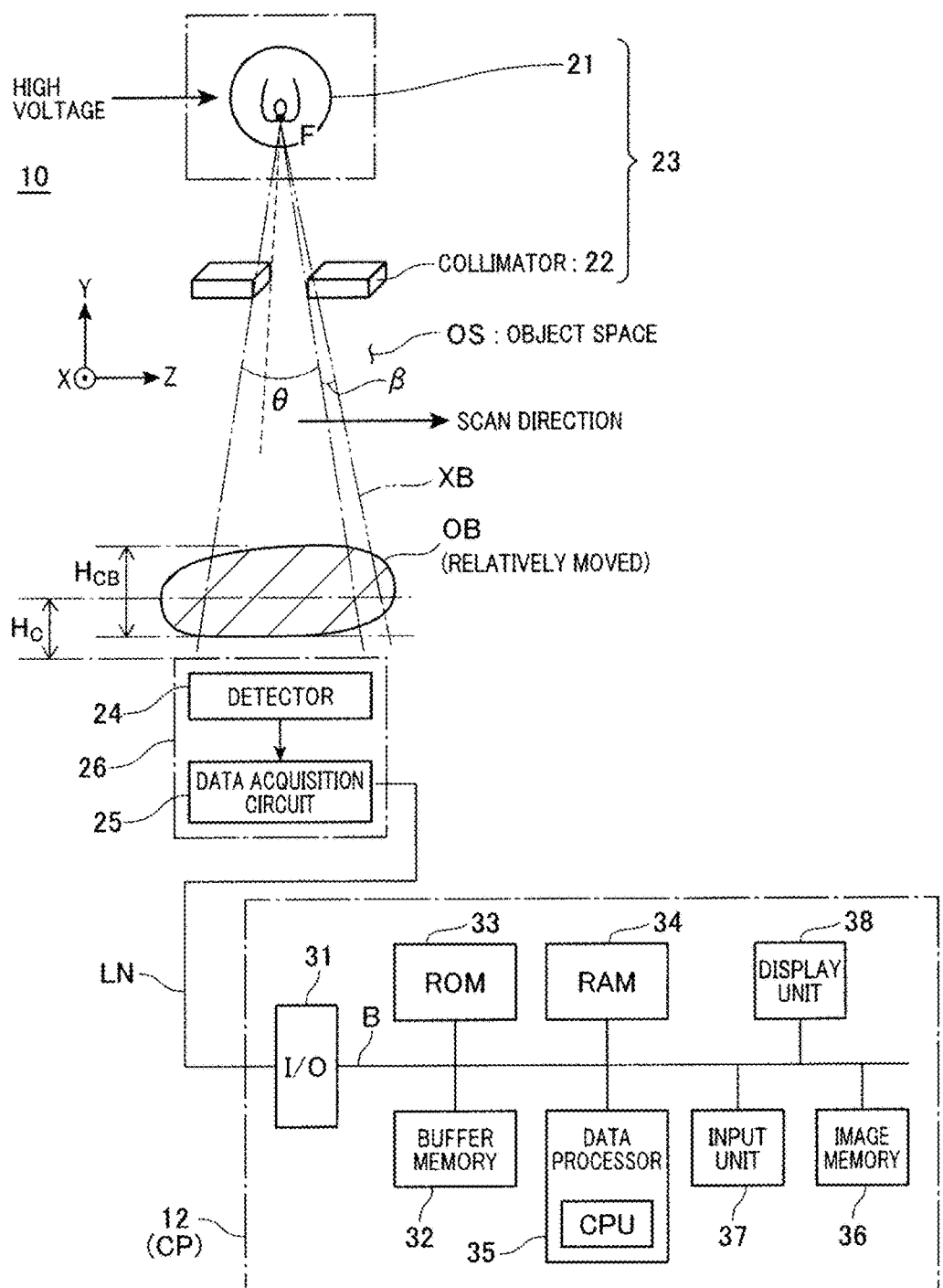
FIG. 1 is a block diagram outlining an X-ray examination system provided with a data processing apparatus according to an embodiment.

First of all, with referring to FIGS. 1 to 15, as one embodiment, a data processing apparatus and a data processing method for X-ray examination according to a mode of the present invention will now be described. FIG. 1 outlines the configuration of an X-ray examination system 10 (an X-ray examination apparatus). In the present embodiment, the data processing apparatus and a data processing method will now be focused on, in which known configurations of this X-ray examination system 10 are simplified in explanations thereof.

Although a data processing apparatus 12 is communicably connected to this X-ray examination system 10 via a communication line LN, this data processing apparatus can be incorporated in the X-ray examination system 10, for example, together with a control portion of this system 10. Alternatively, the data processing apparatus 12 can be provided as a sole component separated from the system 10.

The X-ray examination system 10 is employed as, for example, an X-ray nondestructive inspection system or a medical X-ray panoramic radiography system. An object being examined by this X-ray examination system 10 ranges widely, such as food, industrial products, or patients' breasts. A more easily comprehensive example of this system is an in-line food inspection apparatus used to inspect whether or not food (e.g., vegetables such as sausages or peppers) contains foreign matter, but is not always confined to this example. Besides being these examples, the food may be exemplified as fresh fish, and in such a case, the fish are subjected to inspection of whether or not foreign matter such as fishhooks is left in the fish. In other words, if interpreting the meaning of the foreign matter in other ways, this examination system can be applied to estimation of properties of various items, including checking a content ratio of fat in a block of edible meat block, a mixture of foreign matter or bones in a block of edible meat, and a content of voids or water in wood. For industrial products, the system can be applied to checking of various kinds, including checking mounted states of electric substrate parts or contact states within soldered bumps. In mammography for medically checking human breasts, the system can be used for detecting lesions such as calcification and/or masses in the breasts or determining a content rate of mammary glands at higher accuracies.

In preforming the nondestructive inspection or the X-ray panoramic radiography, the data processing apparatus and the data processing method for X-ray examination according to the is embodiment are operative based on absorption information (or attenuation information) of X-rays when the X-rays are transmitted through a substance, and process such information so as to identify (or determine, distinguish, detect, or decide) the type or properties (physical aspects or states) of the substance. This process is a basic factor of this system. In the following description, this process is called "substance identification" as a whole, if desired.

As shown in FIG. 1, the X-ray examination system 10 has an object space OS in which X-, Y- and Z-axes are set for an orthogonal coordinate system. For nondestructive inspection, the system 10 is provided with an X-ray generator 23 with an X-ray tube 21 and a collimator 22. The X-ray generator 23 generates X-ray beams into the object space OS, in which the X-ray beams have a preset cone angle θ in a scan direction (the Z-axis direction) and a preset fan angle β in a direction (the Y-axis direction) along a section (an XY plane) perpendicular to the scan direction. The X-ray tube 21 has a spot-shaped X-ray focal point F (having a radius of for example 1.0 mmϕ) and is constructed in a rotating anode X-ray tube, for instance. To this X-ray tube 21, a driving high voltage is supplied from a not-shown X-ray high voltage generator for X-ray radiation.

The X-ray examination system 10 is also provided with an X-ray detector 24 (hereinafter simply referred to as a detector) movably arranged so as to be opposed to the X-ray tube 21 with a predetermined distance apart therebetween. The detector 24 is configured by linearly connecting a plurality of modules and, due to this connection, as a whole, the detector 24 has a thin and rectangular X-ray incidence window. Each of the modules is formed as, what is called, a direct conversion type of X-ray detecting member which directly converts X-rays to electrical signals. Each module has a detection layer composed of a semiconductor material, such as CdTe or CZT, in which, for example, 20×80 pixels (each pixel has a size of 0.2 mm×0.2 mm) are formed on the detection layer. Though not shown, on both sides of the detection layer having the plural pixels, charging and collecting electrodes are arranged for applying a bias voltage between the electrodes.

Figure 2:
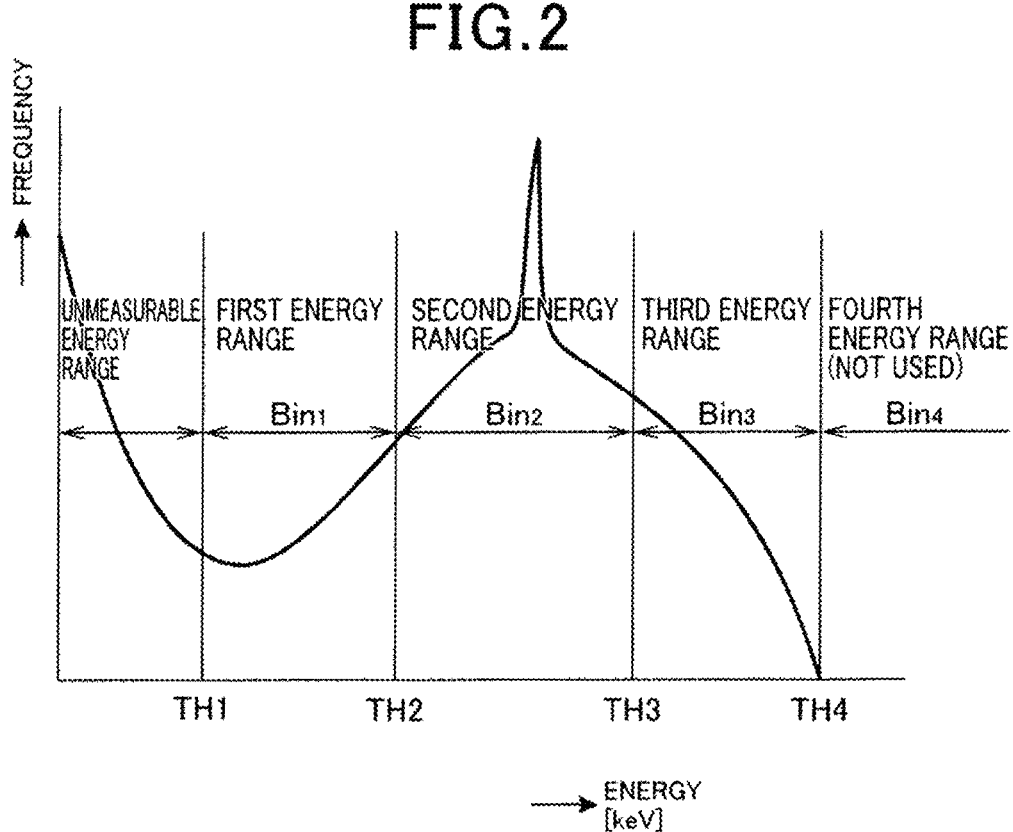
FIG. 2 is a graph exemplifying energy ranges which are set for a photon counting detector and an X-ray energy spectrum.

This detector 24 is a photon counting detector (a photon counting type of detector), which regards X-rays as an aggregate of photons having various energies and is capable of detecting of measuring the number of photons of the X-rays for every energy range of the X-rays. As shown in FIG. 2, the energy ranges are set for example as four energy ranges $Bin_1$ to $Bin_4$. The number of energy ranges is not limited to four, and may be any number chosen as two or more regions.

By this detector 24, X-ray intensities are detected as digitized counts (integrated numbers) showing the number of photons at intervals, at every pixel and in every energy range Bin. When a signal photon impinges into one pixel, an electric pulse signal is generated at this pixel, whose wave height depends on the energy amount of that photon. The wave height of this electric signal, that is, an energy amount, is distributed to a corresponding energy range Bin, in which the count increases by one. The counts in the respective energy ranges Bin are acquired as their accumulated amounts (in the digital signal form) at the respective pixels.

This acquisition process is performed by a data acquisition circuit 25 incorporated as an ASIC layer under the detection layer of the detector 24. The detector 24 and the data acquisition circuit 25 configure a detection unit 26. It is therefore possible that the detection unit 26, practically the data acquisition circuit 25, sends X-ray transmission data (in the form of frame data) at a designated frame rate, to the data processing apparatus 12.

The X-ray examination system 10 having this configuration is exemplified in publications of, for example, JP-A 2007-136163, WO 2007/110465 A1, and WO 2013/047778 A1. In addition, the foregoing photo counting detector 24 is also exemplified by WO 2012/144589 A1.

In cases where this X-ray examination system 10 is used for a dental X-ray panoramic radiography for instance, the object OB being examined is a patient's head. In such a case, the pair of the X-ray generator 23 and the detector 24 is moved around the head so as to rotate on a rotation axis which is defined for example as a head center which is a line in the X-axis direction. This scanning structure for the X-ray panoramic radiography is also shown in JP-A 2007-136163, by way of example.

Further, the data processing apparatus 12 is configured to receive, via the communication line LN, the X-ray transmission data (i.e., frame data) from the X-ray examination system 10. This data processing apparatus 12 can be provided as either an apparatus or an inspection system which is integral with the X-ray examination system 10. Additionally, when the data processing apparatus 12 is communicably connected to the X-ray examination system 10 as shown in this embodiment, the connection may be established in either always-on connection or whenever necessary. The data processing apparatus 12 may be provided as a stand-alone form.

As detailed later, the data processing apparatus 12 is configured to process the received X-ray transmission data in order to provide information inherent to the types or properties of substances which compose an object itself and/or substances present in a region of interest of an object, and further, to test whether or not other substances such as foreign matter are mixed with an object.

[Acquisition of Inherent Information to Substance and Details of Data Processing]

Hereinafter, the data processing apparatus 12 will be detailed in its structure and action, together with a scheme for acquiring the inherent information of substances, which is one of the features of the present information.

The data processing apparatus 12 is configured, by way of example, as a computer system CP. This computer system CP itself is may be a computer system having known calculation functions, in which an interface (I/O) 31 is provided which is connected to the detection unit 26 via the communication line LN. To the interface 41, via internal buses B, a data processor 35 (simply, a processor or a computer) equipped with a buffer memory 32, a ROM (read-only memory) 33 (which foundations as a non-transitory computer readable medium), a RAM (random access memory) 34, and a CPU (central processing unit); an image memory 36; an input unit 37; and a display unit 38 are communicably connected with each other.

The ROM 33 is provided to previously memorize computer-readable programs for identifying substances, which enables the data processor 35 to read the programs and store them in its work area for execution. The data processor 35 is a CPU dedicated to image processing. The buffer memory 32 is provided to temporarily memorize the frame data sent from the detection unit 26. The RAM is provided to temporarily memorize data required during processing of the data processor 35.

The image memory 36 is provided to store therein various image data and various kinds of information processed by the data processor 35. The input unit 37 and the display unit 38 function as a man-machine interface with users, in which the input unit 37 receives input information given by users and the display unit 38 presents images and others under control of the data processor 35. The interface 31, the input unit 37, and the display unit 38 configure an interface section which acquires information from the outside (for example, information given by users).

Figure 3:
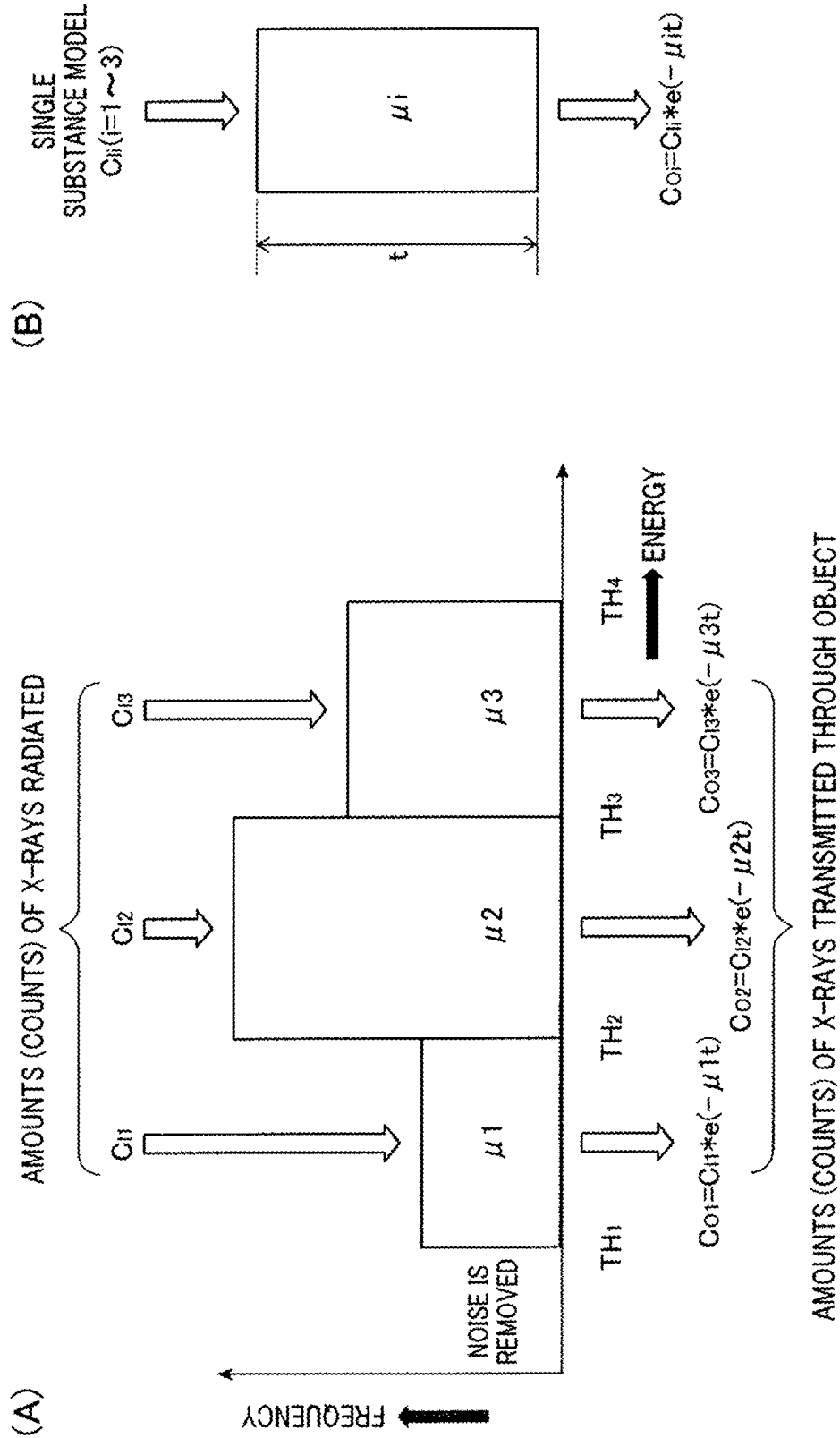
FIG. 3 shows views explaining a relationship between a single substance model and photon counting in each of the energy ranges.
Figure 4:
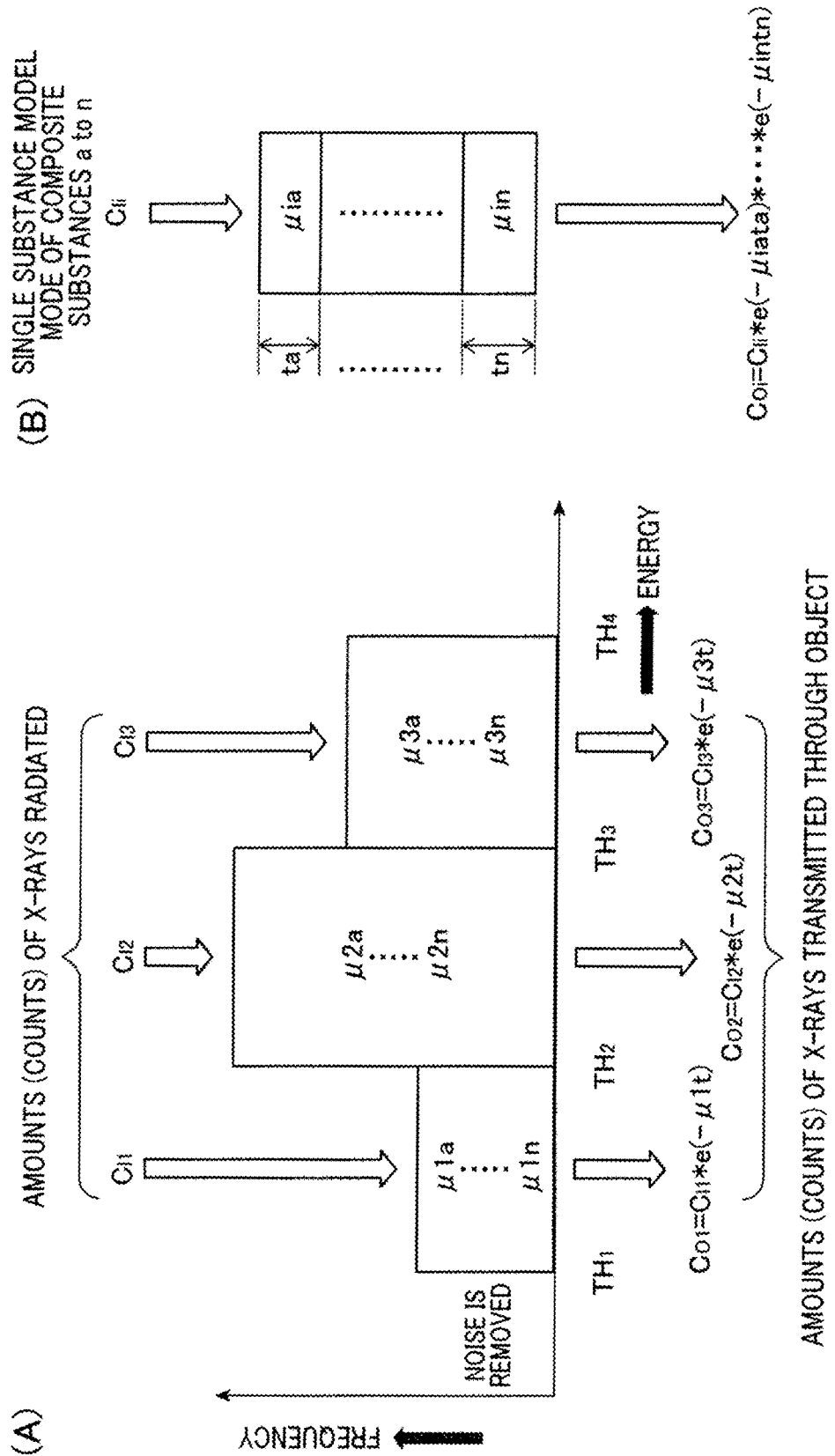
FIG. 4 shows views explaining a relationship between a model composed of a plurality of substances and photon counting in each of the energy ranges.

Relationship Between Data Acquisition and Substance Model on Photon Counting Method With reference to FIGS. 2 to 4, a concept for data acquisition for each substance model will now be described, in which X-rays (fan-shaped X-ray beams), which are radiated from the X-ray tube 21, are transmitted through an object OB and the transmitted X-rays are detected by the detector 24 in the photon counting manner.

FIG. 2 shows a general profile in which the lateral axis indicates amounts of X-ray energy [keV] and the longitudinal axis indicates incidence frequencies (counts) of photons composing the X-rays. In photon counting, as is known, the energy range shown by the lateral axis is divided into a plurality of energy ranges Bin so that thresholds TH are set to the lateral axis. In the example shown in FIG. 2, four thresholds $TH_1$, $TH_2$, $TH_3$ and $TH_4$ are set in the form of suitable reference voltage values applied to comparators (not shown), whereby the first to third energy ranges $Bin_1$, $Bin_2$, and $Bin_3$ are set as usable ranges. Incidentally, energy amounts lower than the first energy range Bin1 fall into unmeasurable energy range due to much noise, while the fourth energy range $Bin_4$ upper than the largest threshold $TH_4$ is not used because this range Bin4 is not related to counting the photons. As a result, in this example, the three energy ranges Bin1, Bin2 and Bin3, which are the first to third energy ranges and which exclude the lowest and highest energy ranges, are used for the photon counting.

The shape of a frequency profile shown in FIG. 2 is decided by the type of material composing the anode of the X-ray tube 21 and voltage applied to the tube, and, as a typical example shown, the counts in the second energy range Bin2 are the largest. Hence, the thresholds TH are decided in appropriate consideration for a balance among the values (i.e., frequencies or counts) counted in the respective energy ranges. These four thresholds $TH_1$ to $TH_4$ are set as voltage thresholds applied to each comparator assigned to each pixel of the detector 24 in the ASIC structure configured as the data acquisition circuit 25. Accordingly, the X-ray photons are counted every pixel and every energy range. As a modification, any number of 3 or more can be adopted as the number of thresholds TH assigned to each pixel. If the number of thresholds TH is three, the number of usable energy ranges is two.

In producing X-ray transmissive images (density images), various modes can be adopted. Count information is obtained at each of the pixels forming the X-ray incidence window of the detector 24 and in each of the energy range Bin. Hence, by multiplying a count at each pixel in each energy range Bin by appropriately chosen weighting coefficients and performing a shift and add process with the multiplied counts, X-ray transmission data (frame data) for each energy Bin can be obtained. In this process, any two or all among the three energy ranges Bin1 to Bin3 are selected, and the counts in such selected energy ranges can be subjected to multiplication of appropriately chosen coefficients and then to the shift and add computation, thereby producing one frame of X-ray transmissive data.

In this way, the energy information depending on the number of X-ray photons is collected at each of the pixels and in each of the energy ranges Bin. It is therefore possible to use the collected energy information in image formation or in other processes with consideration of a contribution of photon energies to the pixels. Further, depending on applications, any energy-weighted image can be produced, thus providing advantages over the convectional integration-type of X-ray remissions data acquisition.

In applying the photon counting technique to the substance identification according to the present application, it is reasonable to take it into account that a substance is composed of a single tissue or a plurality of tissues, and in each case, take X-ray absorption rates of the respective tissues into account. This is because a substance present in a region being examined of an object OB may be tissue composing the object itself or may be another substance other than the substance composing the object.

(i) In case a substance is composed of a single tissue (a single substance model):

In the single substance model, as shown in FIG. 3(A), there are provided ray attenuation coefficients $\mu_1$, $\mu_2$, and $\mu_3$ (cm$^{-1}$) representing the first to third energy ranges $Bin_1$ to $Bin_3$, respectively. The ray attenuation coefficients are indices inherently indicating X-ray transmission properties of a substance.

When X-rays enter a substance, whose thickness is a thickness t (cm), having ray attenuation coefficients $\mu_1$, $\mu_2$, and $\mu_3$ which differ from each other among the energy ranges Bin, a substance model is represented as shown in the figure. Practically, the amounts (i.e., the number of photons $C_{I1}$, $C_{I2}$, and $C_{I3}$ of incident X-rays are subjected to attenuation depending on both the thickness t and the ray attenuation coefficients $\mu_1$, $\mu_2$, and $\mu_3$, respectively, and the amounts (i.e., the number of photons) of the output X-rays can be represented by:

$$C_{o1} = C_{I1} \times e^{-\mu_1 t}$$

$$C_{o2} = C_{I2} \times e^{-\mu_2 t}$$

$$C_{o3} = C_{I3} \times e^{-\mu_3 t} \quad (1).$$

Hence, for the signal substance model composed of a single type of tissue, as shown in FIG. 3(B), responsively to the incidence of X-ray amounts $C_{Ii}$ (the number of photons) to the substance of a ray attenuation coefficients $\mu_i$, and a thickness t, the output X-ray amounts (the number of photons) can be represented by:

$$C_{oi} = C_{Ii} \times e^{-\mu_i t}$$

$$(i=1\sim3) \quad (2).$$

(ii) In case a substance is composed of a plurality of tissues (a plural-substance model):

For the plural-substance model, from a viewpoint of X-ray absorption, as shown in FIG. 4(B), it can be presented that the substance is formed to have a layer structure composed of a layer having a thickness $t_a$ and ray attenuation coefficients $\mu_{ia}$, a layer having a thickness $t_b$ and a ray attenuation coefficients $\mu_{ib}$, . . . , a layer having a thickness $t_n$ and ray attenuation coefficients $\mu_{in}$ are layered on one another. Hence, it is said that, as shown in FIG. 4(A), the first to third energy ranges $Bin_1$ to $Bin_3$ are represented respectively, in terms of X-ray attenuation, by ray attenuation coefficients $\mu_{1a}, \ldots, \mu_{1n}; \mu_{2a}, \ldots, \mu_{2n}; \mu_{3a}, \ldots, \mu_{3n}$ (cm$^{-1}$). When X-rays enter this layered substance, which has the ray attenuation coefficients $\mu_{1a}, \ldots, \mu_{1n}; \mu_{a2}, \ldots, \mu_{2n}; \mu_{3a}, \ldots, \mu_{3n}$ which are different from each other for the respective energy ranges Bin and which has the layer thicknesses $t_a, \ldots, t_n$, (cm), can be modeled as shown in the figure. In other words, the incident X-ray amounts (the number of photons) $C_{I1}$, $C_{I2}$, and $C_{I3}$ are attenuated depending on the ray attenuation coefficients $\mu_{1a}, \ldots, \mu_{1n}; \mu_{2a}, \ldots, \mu_{2n}; \mu_{3a}, \ldots, \mu_{3n}$ and the thicknesses $t_a, \ldots, t_n$, and their outputted X-ray amounts (the number of photons) can be represented by:

$$C_{o1} = C_{I1} \times e^{-\mu_{1a} t_a} \times \ldots \times e^{-\mu_{1n} t_n}$$

$$C_{o2} = C_{I2} \times e^{-\mu_{2a} t_a} \times \ldots \times e^{-\mu_{2n} t_n}$$

$$C_{o3} = C_{I3} \times e^{-\mu_{3a} t_a} \times \ldots \times e^{-\mu_{3n} t_n} \quad (3).$$

It is thus possible to represent the plural-substance model composed of a plurality of compositions such that, as shown in FIG. 4(B), when receiving incidence of X-ray amounts $C_{Ii}$ (the number of photons), the outputted X-ray amounts (the number of photons) are defined as:

$$C_{oi} = C_{Ii} \times e^{-\mu_{ia} t_a} \times \ldots \times e^{-\mu_{in} t_n}$$

$$(i=1\sim3) \quad (4)$$

[Processing Procedures]

On the assumption the photon counting and the ray attenuation amounts $\mu t$ are related to each other based on the foregoing substance model, a process for substance identification, which is executed by the data processing apparatus 12, will now be described. In the data processing apparatus 12, the data processor 35 is configured to perform preassigned programs, thus providing the substance identification which is according to a procedure shown in FIG. 5.

[Preprocessing]

First, the data processor 35 determines whether or not it is necessary to acquire images, for example, automatically or interactively with a user (step S1), and waits for the timing of the image acquisition. When it is determined that the image acquisition is necessary (YES at step S1), the data processor reads frame data previously stored in the buffer memory 32 and places it in the RAM 34 for example (step S2). Pictorially shown in FIG. 6, the frame data are composed of i) three frame data $FD_1$, $FD_2$ and $FD_3$ each consisting of the counts of the X-ray photons whose energy amounts belong a corresponding one of the three energy ranges $Bin_1$, $Bin_2$ and $Bin_3$ and ii) a frame data $FD_{all}$ consisting of the counts of the X-ray photons whose energy amounts belong to an all energy range Bin_all ($Bin_1 + Bin_2 + Bin_3$).

The data processor 35 then determines whether or not the substance identification should be executed, in response to an automatic instruction or interactive instructions with a user (step S3). The data processor waits for a command to start the substance identification, and will end this process when receiving an end instruction with no execution of the substance identification (step S4).

[Production of Focused Images]

When the data processor 35 determines execution of the substance determination at step S3 (YES at step S3), the processor then designates a section, for example, which intersects with an object OB being examined, automatically or interactively with the user (step S5).

By way of example, in interactively designating a position of the section, a user can use the input unit 37 to specify a height $H_C$ from the detector 24, as shown in FIG. 1. For example, if it is known that the height of the object OB put on the conveyance belt (not shown) in the height direction (the Y-axis direction) in FIG. 1 is $H_{OB}$ or more, the section at a height $H_C$ approximately equal to the center of the object OB in the height direction may be designated. Of course, in this example, the detection unit 26 is located under the conveyance belt, so that the height $H_C$ is designated by taking it account a gap between the conveyance belt and the detection surface of the detector 24 of the detection unit 26. In cases where the height of the object is unknown or has irregularities, the height $H_C$ may be set to be equal to the upper surface of the conveyance belt. Alternatively, at the entrance of the conveyance belt, there can be provided a device for sensing the height of the object OB, which is for example an optical device, thereby providing height information.

Meanwhile, in automatically designating the section of the object OB, the specified information indicating a section at step S5 is not for the height $H_C$, but is for setting an all-pixel focused plane an image along which is focused pixel by pixel. In this case, the height of the all-pixel focused plane is not always constant (flat), but is irregular, in many cases, where the height intersects with the object OB but, when seen finely, the pixels may have different heights, on account of being optimally focused at each pixel. The scheme for producing the all-pixel focused plane is exemplified by for example U.S. Pat. No. 8,433,033 and PCT/JP2010/62842. The scheme according to such exemplifications uses a laminography (or called a tomosynthesis technique).

After this setting of the section, the data processor 35 produces a tomographic image at the designated section, by using a plurality of frame data $FD_{all}$ derived from the all energy range Bin_all, for instance (step S6).

This image production is performed such that, if a constant height $H_C$ has been designated, the plurality of frame data $FD_{all}$ are overlapped on one another and subjected to pixel value addition at the respective pixels, with being shifted by a shift amount corresponding to the height $H_C$ after each addition, which are main processes in the laminography. This way produces a tomographic image (a laminography image) $IM_{all}$ whose optimum focusing height position is fixed to the designated height $H_C$ (refer to FIG. 6). Though being limited to the height $H_C$ in the focusing height position, this image $IM_{all}$ is one type of focused images.

Figure 6:
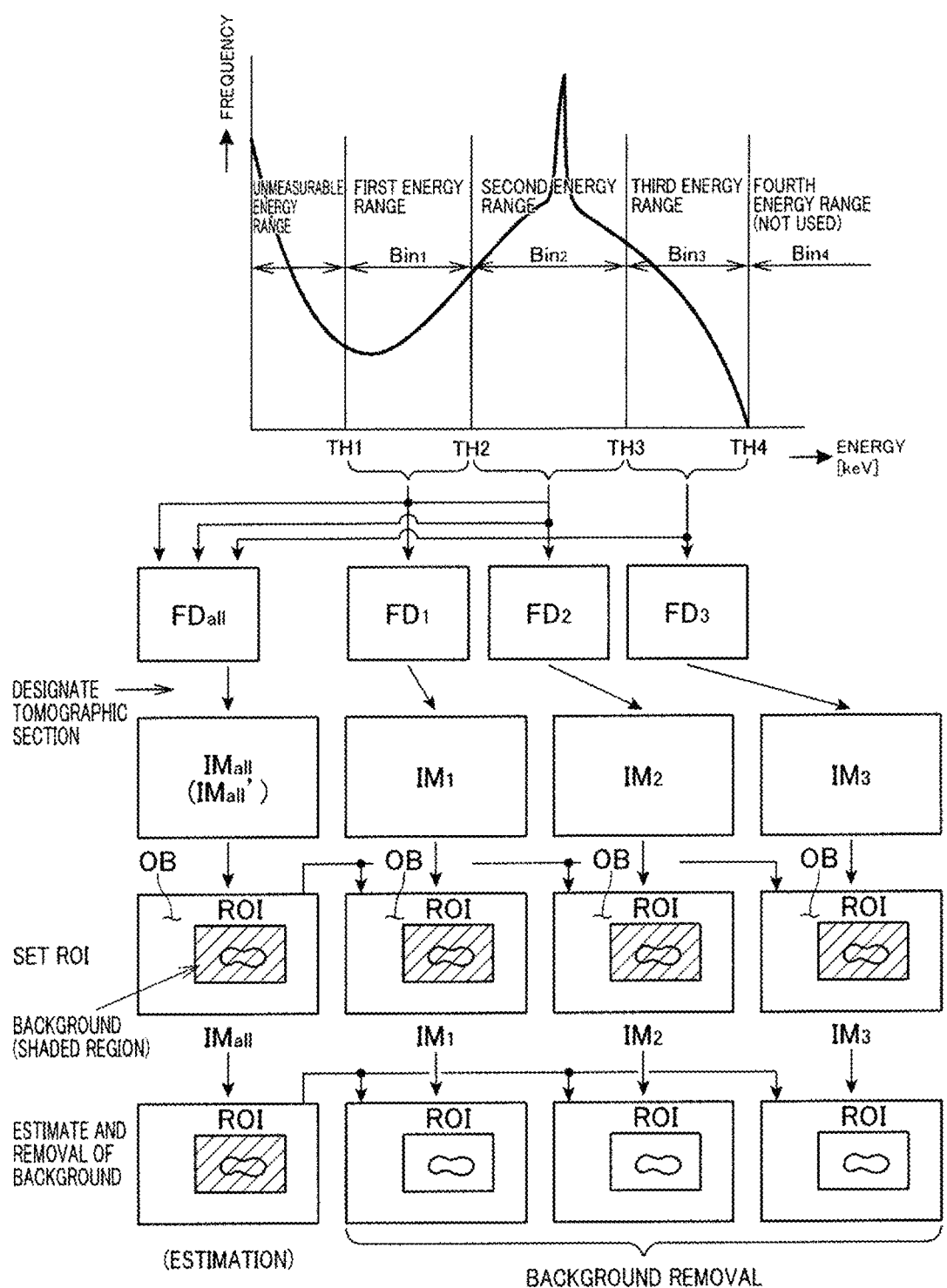
FIG. 6 is an illustration explaining pre-processing for the substance identification performed by the data processor.

Alternatively, when setting of an all-pixel focused plane of the object OB is ordered, a plurality of frame data $FD_{all}$ derived from, for example, the all energy region Bin_all among the collected frame data are used to produce an all-pixel focused image $IM_{all}'$ in the laminography technique (refer to FIG. 6). The object OB is depicted in this all-pixel focused image $IM_{all}'$, which is a tomographic image optimally focused pixel by pixel in the height direction or the X-ray radiating direction. This tomographic image is exemplified in U.S. Pat. No. 8,433,033 and PCT/JP2010/62842, using the same method as described before. These known publications show examples of dental applications, and, by converting a pseudo three-dimensional curved image produced according to this known techniques to a two-dimensional image, the converted two-dimensional image is available in the present embodiment as a two-dimensional focused tomographic image. This two-dimensional tomographic image is finer in focusing levels than the focused image $IM_{all}$ obtained at the constant (flat) height described before, thanks to the focusing process applied to each pixel. Any type of focused image is usable in the present embodiment, so that, in the following, the foregoing various focused images are simply referred to as a focused image $IM_{all}$.

The data processor 35 then uses the frame data $FD_1$, $FD_2$, $FD_3$ acquired in the three energy ranges $Bin_1$, $Bin_2$ and $Bin_3$ to consecutively produce tomographic images with the laminography technique, where the tomographic images are made at the designated height $H_C$ or an average height of, for example, the all-pixel focused plane (steps S7, S8 and S9). By this, as pictorially shown in FIG. 6, three focused images $IM_1$, $IM_2$ and $IM_3$ are reconstructed for the three energy ranges. These three focused images $IM_1$, $IM_2$ and $IM_3$ can be reconstructed in any sequential order. Of course, these three focused images $IM_1$, $IM_2$ and $IM_3$ can be produced as all-pixel focused images which have been explained.

[Setting Region of Interest]

Then, on the all-pixel focused image $IM_{all}$, the data processor 35 sets a region of interest ROI automatically or interactively with the user (step S10). When, for example, it is desired to identify the type of a substance composing the object OB, the region of interest ROI is set to have an appropriate size which can encircle an area of the object OB in the focused image $IM_{all}$, on the assumption that the area is composed of only the same type of substance(s). The thickness of such an area may be changed positionally. On the other hand, in detecting foreign matter or identifying a lesion, the region of interest ROI is set to have a size which can encircle a doubtful area for foreign matter or a medically interceded area (refer to FIG. 6).

When the region of interest ROI has been decided on the all-pixel focused image $IM_{all}$, information indicative of this region is used to set this region of interest ROI on each of the three focused images $IM_1$, $IM_2$ and $IM_3$ in the same way as above (refer to FIG. 6).

[Estimation and Deletion of Background]

Then, on the focused image $IM_{all}$, the data processor 35 estimates pixel components (background components) which compose a background of the region of interest ROI (step S11). These background components depend on what kind of information is desired to be identified, as explained. In identifying or determining the type(s) or properties of a substance(s), the background components are known components of carrying means including the conveyance belt and the air, in many cases. In identifying (or estimating) the type(s) of foreign matter or states of a lesion, the background components include, in addition to the foregoing known components, components of the object OB itself. If the background components are known, a fixed value corresponding to such background components is subtracted from the pixel values forming the region of interest ROI on the three focused images $IM_1$, $IM_2$ and $IM_3$ for the respective energy ranges (step S12).

In contrast, if amounts of the background components are unknown, it is necessary to estimate the amounts thereof. As this is estimation technique, appropriate techniques, such as an interpolation technique which uses values of pixels at mutually separated plural locations outside the region of interest, can be employed.

The foregoing pre-processing is mainly intended to set the region of interest ROI on each of the focused images $IM_1$, $IM_2$ and $IM_3$ obtained from the three energy ranges and remove the background components from those images. It is therefore possible to perform the preprocessing with any of the focused images $IM_1$, $IM_2$ and $IM_3$, in place of producing the all-pixel focused image $IM_{all}$ obtained from all the energy ranges.

[Main Process for Substance Identification]

After the preprocessing, the data processor 35 performs a main process for the substance identification (step S13). This main process is shown in FIG. 7.

<Calculation of Ray Attenuation Value μt>

First, in the data processor 35, values of pixels which are encircled by the region of interest ROI on the three focused images $IM_1$, $IM_2$ and $IM_3$ and from which the background components are removed are used to ray attenuation values μt (step S131 in FIG. 7). The symbol μ indicates a ray attenuation coefficient (simply referred to as an attenuation coefficient) of a substance and the symbol t indicates the thickness of the substance along a radiation direction of X-ray beams transmitting through the substance.

Using the foregoing single-substance and plural-substance models, the ray attenuation value μt can be calculated, every pixel, in each of the energy ranges Bin, (i=1 to 3) on the basis of the following formulae.

$$\mu_i t = \ln Cl_i - \ln Co_i \tag{5}$$

($i = 1$ to 3: in case of the single-substance model)

[formula 1]

$$\sum_{j=a}^{n} \mu_{ij} t_i = \ln Cl_i - \ln Co_i \tag{6}$$

($i = 1$ to 3, $j = a$ to $n$: in case of the plural-substance model)

The symbol "ln" in the formulae shows the computation of natural logarithm.

From these formulae, it is understood that, if the number of photons which have entered a substance and the number of photons which have outputted therethrough are known, the ray attenuation value μt can be calculated. The number of outputted photons, $Co_i$, is detected, pixel by pixel, as the number of photons by the detector 24 in each of the energy ranges. The symbol, $CI_i$, indicates the number of incidence photons under the same conditions as those in actual X-ray examinations, and is a known value which can be preset. Of course, when necessary, the number of incidence photons can be estimated for the substance identification, with consideration for differences in actual X-ray conditions.

In the medical examinations, soft tissue of human breasts or limbs may be regarded as being composed of substances which can structurally be simplified. Moreover, devices to pressing or fixing a human part being imaged in the examinations are plate-shaped, with the result that the ray attenuation value $\mu t$ can be calculated accurately. Similarly, in nondestructive inspections for food or other items, as long as it is possible to estimate the background components as described above, the ray attenuation value $\mu t$ can be calculated accurately based on information of pixels from which the background components were removed.

Then, from each of the focused images $IM_1$ to $IM_3$ for the foregoing three energy regions $Bin_1$ to $Bin_3$, the data processor 35 extracts the ray attenuation values $\mu t$ of the respective pixels composing the region of interests, ROI, and vectorizes the extracted values (step S132: refer to FIG. 8).

Practically, the data processor 35 produces a three-dimensional ray attenuation vector ($\mu_1 t$, $\mu_2 t$, $\mu_3 t$) at each of the pixels of each of the region of interests (refer to FIG. 8). Since the three-dimensional ray attenuation vectors ($\mu_1 t$, $\mu_2 t$, $\mu_3 t$) still include factors showing the thickness t and the density, these vectors themselves only show X-ray attenuation amounts derived from such thickness t and the density, not showing indexes inherent to a substance(s). The reason is that, similarly to X-ray scanogram or simply X-ray radiography, the thickness is an unknown factor, so that ray attenuation coefficients $\mu_1$, $\mu_2$ and $\mu_3$ inherent to a substance cannot be obtained. Even more, a single three-dimensional ray attenuation vector ($\mu_1 t$, $\mu_2 t$, $\mu_3 t$) is not enough, because this vector is buried in noise components, whereby it is difficult to obtain information inherently identifying a substance.

With consideration of such difficulties, the inventors have found that a substance(s) can be identified if the three-dimensional attenuation vectors ($\mu_1 t$, $\mu_2 t$, $\mu_3 t$) are normalized and treated as a group of such vectors.

Practically, the respective three-dimensional attenuation vectors ($\mu_1 t$, $\mu_2 t$, $\mu_3 t$) are normalized into unit lengths (having a length of 1) according to the following formula (7), thus producing three-dimensional mass attenuation vectors ($\mu_1'$, $\mu_2'$, $\mu_3'$) which exclude the factors of both thickness t and density (step S133).

$$(\mu_1', \mu_2', \mu_3') = (\mu_1 t, \mu_2 t, \mu_3 t)/((\mu_1 t)^2 + (\mu_2 t)^2 + (\mu_3 t)^2)^{1/2} \quad (7)$$

$$= (\mu_1, \mu_2, \mu_3)/(\mu_1^2 + \mu_2^2 + \mu_3^2)^{1/2}$$

As a matter of course, the normalization is to equalize the lengths of the respective three-dimensional mass attenuation vectors ($\mu_1'$, $\mu_2'$, $\mu_3'$), so that the equalized length is not limited to 1, but any length can be adopted. Incidentally, the symbol $\mu$ indicates the ray attenuation coefficient provided before the normalization, while the symbol $\mu'$ indicates the ray attenuation coefficient obtained by the normalization. In addition, attenuation coefficients $\mu$ shown in FIGS. 10, 13, 16, 17, 19, 20 and 23 indicate values obtained by the normalization.

Thus, by the normalization, the factors of both thickness t and density can be deleted from the coefficients, so that the respective mass attenuation vectors ($\mu_1'$, $\mu_2'$, $\mu_3'$) can be presented in a three-dimensional coordinate system such that start points of the respective vectors are put at the coordinate origin (step S134). The three mutually orthogonal axes of this coordinate system are respectively assigned to the ray attenuation coefficients $\mu_1$, $\mu_2$, and $\mu_3$. Hence, the coordinate positions of end points of such respective vectors indicate information inherently indicating a substance(s) (i.e., information showing the type(s) and/or properties of substance(s)).

In the present embodiment, in this way, the vectors showing the X-ray attenuation are treated as the ray attenuation vectors ($\mu_1 t$, $\mu_2 t$, $\mu_3 t$) before the normalization, and treated as the mass attenuation vectors ($\mu_1'$, $\mu_2'$, $\mu_3'$) after the normalization. This vector information is processed three-dimensionally, but may be processed two-dimensionally.

Figure 18:
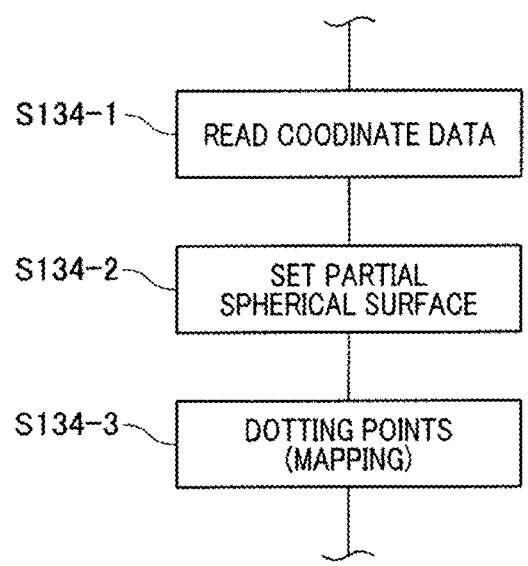
FIG. 18 is a partial flowchart detailing a process of step S134 in FIG. 7 according to the embodiment.

The process at step S134 is performed in the order shown in FIG. 18, for example. That is, mutually-orthogonal three-axis coordinate data corresponding to the ray attenuation coefficients $\mu_1$, $\mu_2$, $\mu_3$, which are previously stored in the ROM 33, are read for producing display space (step S134-1), and a partial spherical surface passing each of the three axes at a length of 1 is set in a memory space (step S134-2). Then, one end of each of the respective three-dimensional mass attenuation vectors ($\mu_1'$, $\mu_2'$, $\mu_3'$) is arranged at the coordinate origin, while the other end, i.e., the tip, of each the vectors ($\mu_1'$, $\mu_2'$, $\mu_3'$) is arranged (dotted or mapped) at an intersecting point with the partial spherical surface (step S134-3).

The three-dimensional gradient information of the three-dimensional mass attenuation vectors ($\mu_1'$, $\mu_2'$, $\mu_3'$), which is replaced by the normalizing formula (7) at each pixel, changes depending on types and/or properties of substances in the three-dimensional space. Thus, this three-dimensional gradient information can also be interpreted as scatter data of energy corresponding to information inherent, in a pseudo (virtually) way, to the substances. By the inventors, the positions pointed by the tips of the three-dimensional mass attenuation vectors ($\mu_1'$, $\mu_2'$, $\mu_3'$), i.e., a set of pieces of information (practically the scattering points) showing the gradients of such vectors is also called a three-dimensional scatter diagram. In other words, depending on substances, the gradients of the three-dimensional mass attenuation vectors ($\mu_1'$, $\mu_2'$, $\mu_3'$) change, whereby thee-dimensional positions (i.e., positions of scattering points) pointed by the vector tips also change. Information of such three-dimensional positions of the vectors reflects energy distributions of the X-ray photons.

In addition, the data processor 35 calculates the lengths of the respective three-dimensional ray attenuation vectors ($\mu_1 t$, $\mu_2 t$, $\mu_3 t$) for each pixel, according to the following formula.

$$((\mu_1 t)^2 + (\mu_2 t)^2 + (\mu_3 t)^2)^{1/2} \quad (8)$$

The amounts rendered by this formula indicate absorption amounts of X-rays which have not been transmitted through a substance, through which part of the X-rays has been transmitted through. Such amounts are also effective as complementary information for the substance identification and can be provided as pixel values composing an image which can be a replacement of the conventional absorption image. Hence, there is produced an image whose pixel values are given by graduating the absorption amounts of the X-rays which have not be transmitted (step S135). By the present inventors, the lengths of the three-dimensional mass attenuation vectors are referred, in a pseudo (or virtual) way, to as "absorption vector lengths", which correspond to X-ray attenuation amounts. An image whose pixel values indicate the absorption vector lengths is referred to an "absorption vector-length image (or a pseudo absorption image)". This absorption vector-length image is not easily dependent on shapes of X-ray incidence energy spectrums, thus providing stable images and reflecting the ray attenuation values µt as a whole. In consequence, the absorption vector-length image provides higher contrast. This absorption vector-length image can be stored in the image memory 36, and can be displayed by the display unit 38 when need rises. In particular, by this absorption vector-length image, distinguishing images are provided to a substance having a larger mass with larger X-ray beam hardening.

Figure 5:
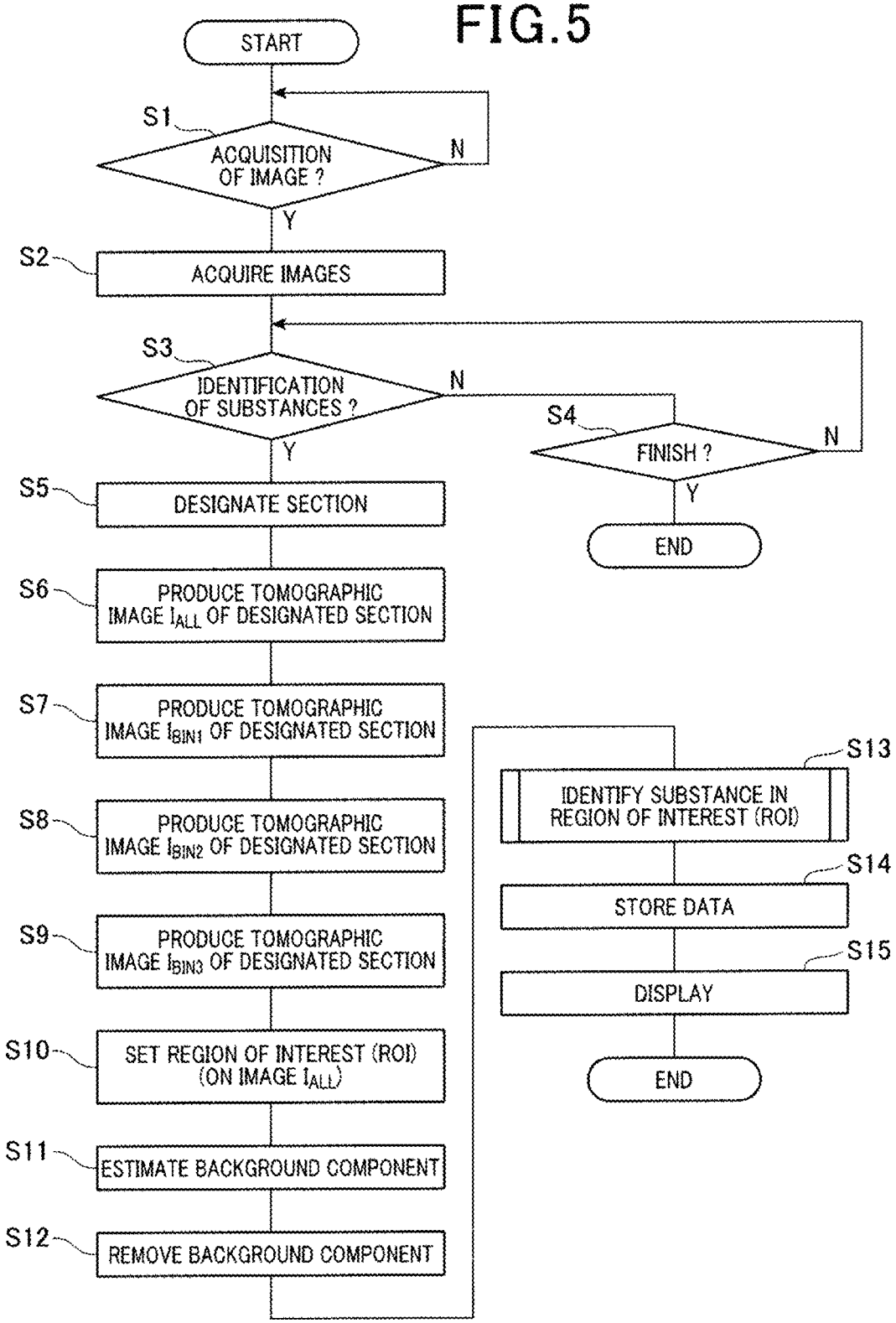
FIG. 5 is a flowchart outlining processing for substance identification and pre-processing thereof, which are performed by a data processor.

Finally the data processor 35 stores, into the image memory 36, data of the foregoing three-dimensional scatter diagram as the substance identification information, and the absorption victor length image as complementary information for the substance identification (FIG. 5, step S14). On command, such images are presented to a user via for example the display unit 38 (step S15).

Accordingly, based on the X-ray photon counts for each of the respective energy ranges, which are detected by the photon counting detector 24, information inherently identifying an object can be obtained, regardless of being how large the thicknesses of objects OB are. This operation can provide greater advances if combined with display and/or analysis of the substance inherent information.

[One Example of Display and Analysis of Substance Inherent Information]

The display and analysis of this substance-inherent information are carried out as one step in, for example, step S15. The data processor 35 responds to instructions from a user, for example, to present the foregoing substance-inherent information. Practically, a spherical surface of radius 1 (i.e., of unit radius) is set in the three-dimensional coordinate system whose three axes are assigned to the normalized ray attenuation coefficients $\mu_1$, $\mu_2$ and $\mu_3$ (refer to FIG. 9, step S31).

A three-dimensional scatter diagram composed of the three-dimensional mass attenuation vectors ($\mu_1'$, $\mu_2'$, $\mu_3'$) for the respective pixels is displayed in the three-dimensional coordinate space, where the vectors start from the origin of the coordinate system and the ends of the vectors are arranged (dotted or mapped), for example, on the single (i.e., the same) spherical surface (whose radius is normalized as the radius of 1). The mapped end points on the spherical surface are aggregated based on substance-inherent information, thus providing aggregations of the scattering points inherent to the substance(s). Hence, even if a substance is assigned to an object, whose thickness t changes among some or all the pixel positions, the scattering points are aggregated independent of the factor of the thickness t.

Figure 10:
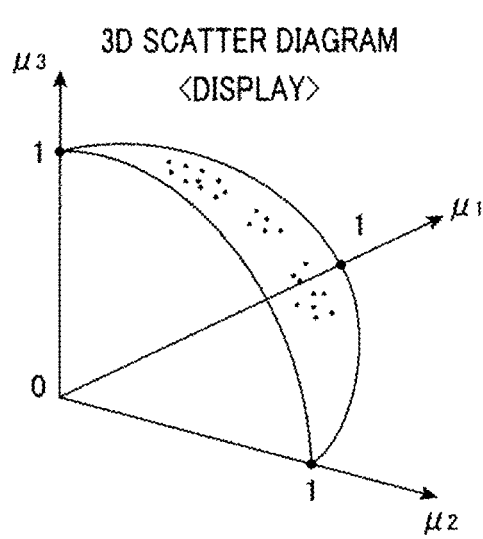
FIG. 10 is a perspective view pictorially explaining a normalized three-dimensional scatter diagram.
Figure 11:
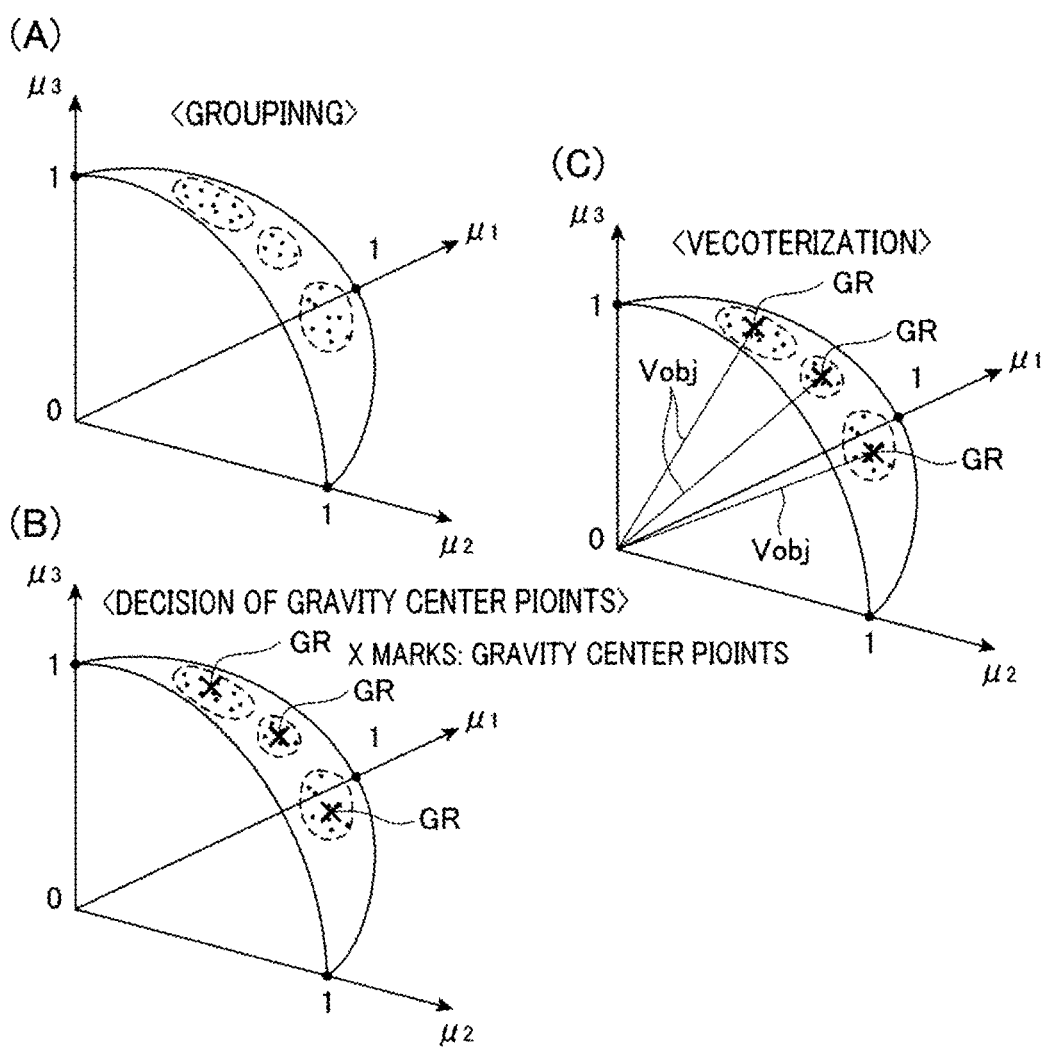
FIG. 11 shows perspective views explaining generation of three-dimensional vectors from the three-dimensional scatter diagram, based on scattering points inherent to a substance.
Figure 12:
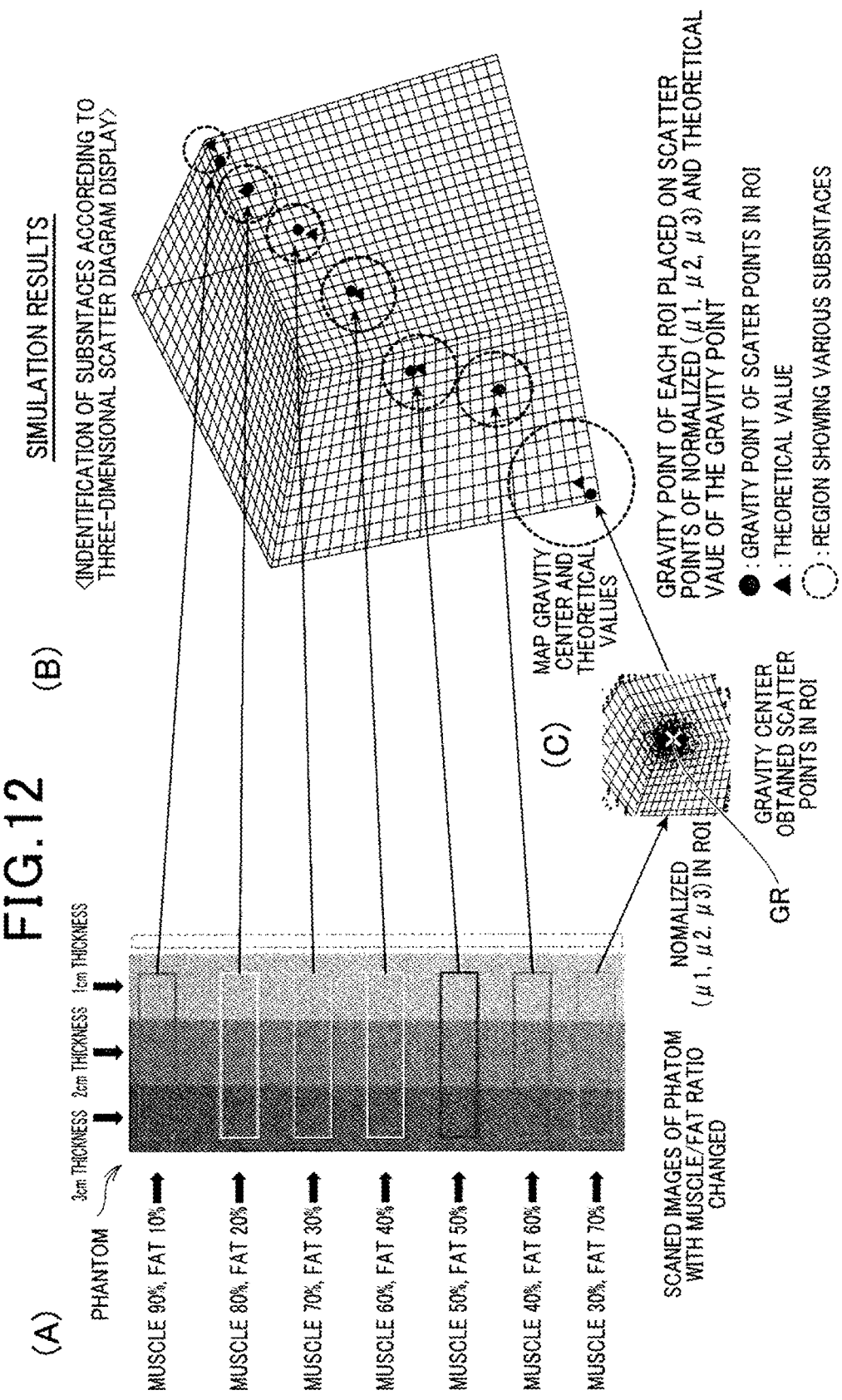
FIG. 12 shows diagrams explaining results of a simulation for verifying the substance identification.

FIG. 10 pictorially shows an example in which the groups of the scattering points are mapped on part of a normalized spherical surface (the part of the same single surface) as three-dimensional scatter diagrams.

As shown in FIG. 11(A), the data processor 35 then groups the scattering points (refer to dotted-lines: step S33), and as shown in FIG. 11(B), calculates positions of the center of gravity GR of the grouped scattering points (step S34). Then, as shown in FIG. 11(C), the data processor 35 calculates vectors Vobj each connecting the origin and each of the positions of the center of gravity GR derived from the respective scattering point groups (step S35).

The data processor 35 then compares the vectors Vobj with predetermined and preset reference data to identify or determine the type and/or properties of a substance(s) (step S36). The reference data includes a memory table, for example, in which three-dimensional gradients of the vectors Vobj are memorized together with their allowances, which gradients were measured beforehand with changing various types and/or properties of reference substances. Accordingly, when it is determined whether each of the calculated vectors Vobj falls into the allowances, the substance(s) can be identified in its type and vector information which is noise is excluded as well. The identified information is preserved (step S36).

Incidentally, at step S15 described, the three-dimensional scatter diagrams and the absorption vector-length image can be presented and provided in other various modes. For example, the data processor 35 is able to display on the display unit 38 both the three-dimensional scatter diagrams and the absorption vector-length image in a separated manner. In such a case, the three-dimensional scatter diagrams may first be displayed, and, responsively to a user's request, the absorption vector-length image may be displayed as an auxiliary image.

[Various Simulations]

In order to verify the validity of the substance identification according to the present embodiment, the inventors simulated various modes, which will now be described.

[1. Simulation to Verify that Differences in Properties of Substance can be Identified]

A first simulation was performed to see how differences in properties of substances changes the three-dimensional scatter diagram, with changing the rates of contents of fat and muscle in a biological phantom and with changing its thickness to 1 cm, 2 cm and 3 cm.

FIG. 12(A) shows a biological phantom. This biological phantom is formed to have strip-shaped portions of thicknesses approx. 3 cm, 2cm and 1cm which are arrayed in one direction. Additionally, along the other direction in each strip-shaped portion, a muscle/fat ratio is changed such that a portion made of muscle 90% and fat 10%, a portion made of muscle 80% and fat 20%, a portion made of muscle 70% and fat 30%, . . . , a portion made of muscle 30% and fat 70% are arrayed. To avoid differences in the densities of a scanned image, the thicknesses are slightly (<<1 cm) adjusted. Adjacently to this biological phantom, an air layer is set as background components. In this example, a statistical amount of photon counts in the air layer is 27,200 counts, a rectangular ROI set on the biological phantom has a size of 288 $mm^2$, and the background area was 189 $mm^2$.

A result of depicting the foregoing three-dimensional scatter diagram of this biological phantom is shown in FIG. 12(B). As shown, it was found such that scattering points are almost separated from each other every ratio of the muscle/fat and the positions of center of gravity (for example, refer to black circles in FIG. 12(C)) in each of the separated scattering points. In addition, when the thickness of the phantom is changed, the scattering points are distributed to be in the same group of the points. Although the origin is not seen in the three-dimensional coordinate depicted in FIG. 12(B), the origin is located apart from this coordinate.

From this simulation, it was found that biological bodies having different muscle/fat ratios (that is, different properties of a substance) are identified as mutually different substances in view of X-ray absorption. Conversely, depicting this three-dimensional scatter diagram, it is possible to estimate a content ratio of muscle/fat. In this simulation, it was found such that an error component is a deviation of a maximum 12% or thereabouts to a distance of 10% difference between the mutually-adjacent fat and muscle, and the ratio of content of the muscle/fat can be identified within ±1.2%, independently of how large the thickness is.

[2. Simulation Verifying that Substances can be Identified by Their Types]

Figure 13:
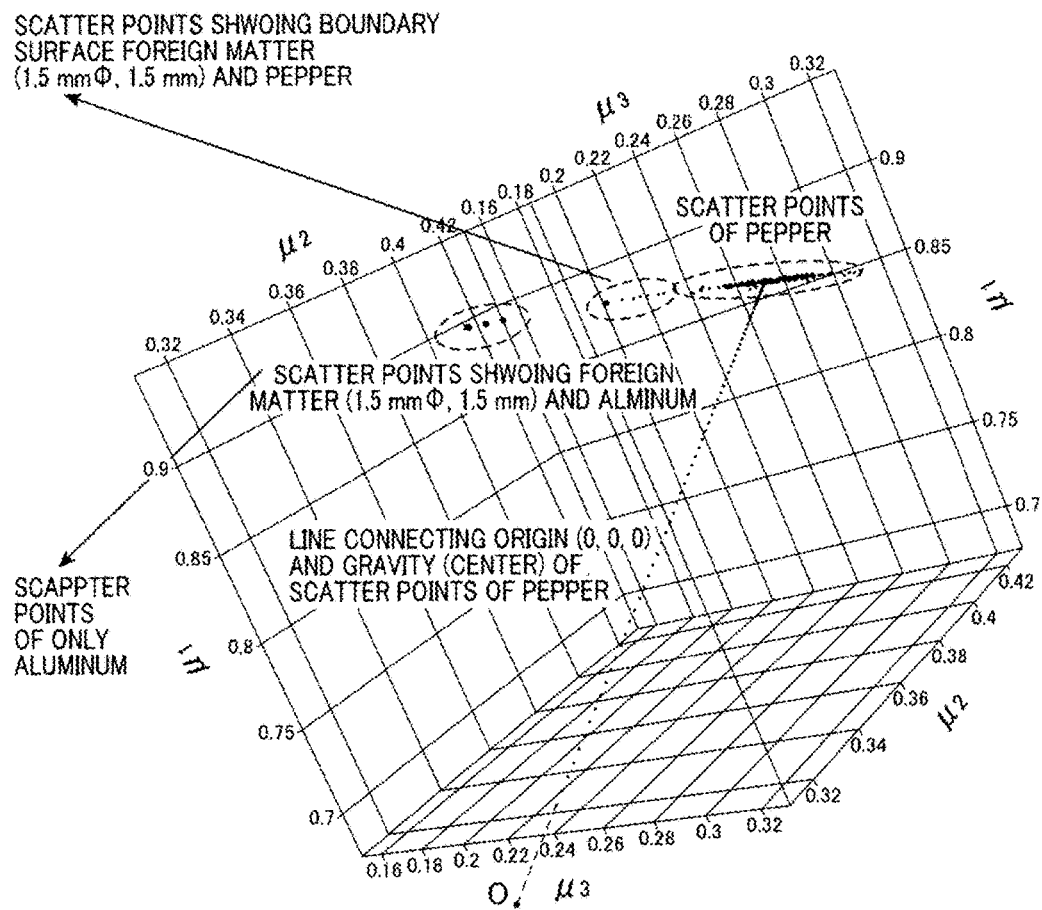
FIG. 13 shows a diagram explaining results of another simulation for verifying the substance identification.

FIG. 13 shows a simulation which verifies that the types of substances can be identified, which was also performed by the inventors. If substances can be identified by their types (kinds), it is possible to determine whether or not the substances contain foreign matter (i.e., a substance having tissue different from that in an object being examined). This fact is useful for X-ray nondestructive inspection.

The inventors made a pepper phantom made of tissue identical to peppers (vegetable) and aluminum (Al) pieces of 1.5 mmφ and 1.5 mm length serving as foreign matter are placed in the tissue.

Using this pepper phantom, the foregoing three-dimensional scatter diagram was depicted as shown in FIG. 13. This depiction confirmed the fact that, by this depiction, there are shown a group of scattering points derived from the tissue itself of the pepper which is an object, a group of scattering points (noise) derived from the boundary between the pepper and the outside thereof, and a group of scattering points derived from the aluminum pieces which are foreign matter.

Hence, as described, the center of gravity of each of the groups composed of the scattering points is positionally decided, a vector connecting the origin of the three-dimensional coordinate and the center of gravity is produced, and the three-dimensional gradient of this vector is compared with reference data, i.e., gradient. These steps enable checking of whether or not there foreign matter in an object, and, if such a matter is contained, to confirm that the foreign matter is an aluminum piece. If there is no aluminum piece in the object, there appears no group of corresponding scattering points in the three-dimensional scatter diagram.

[3. Simulation Verifying Advantage of Absorption Vector-Length (Pseudo Absorption) Image]

Figure 14:
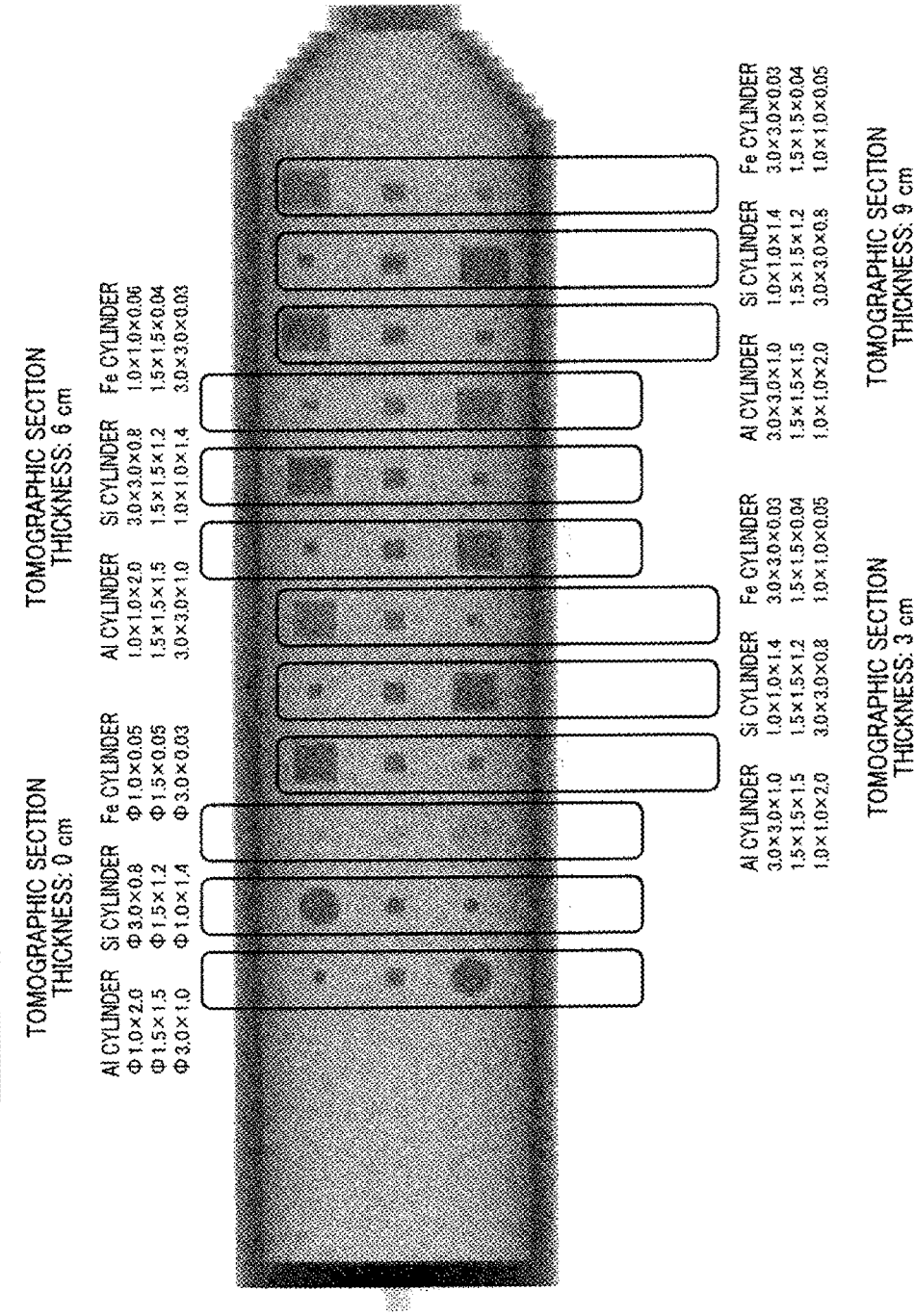
FIG. 14 shows a diagram explaining results of another simulation for verifying the substance identification.
Figure 15:
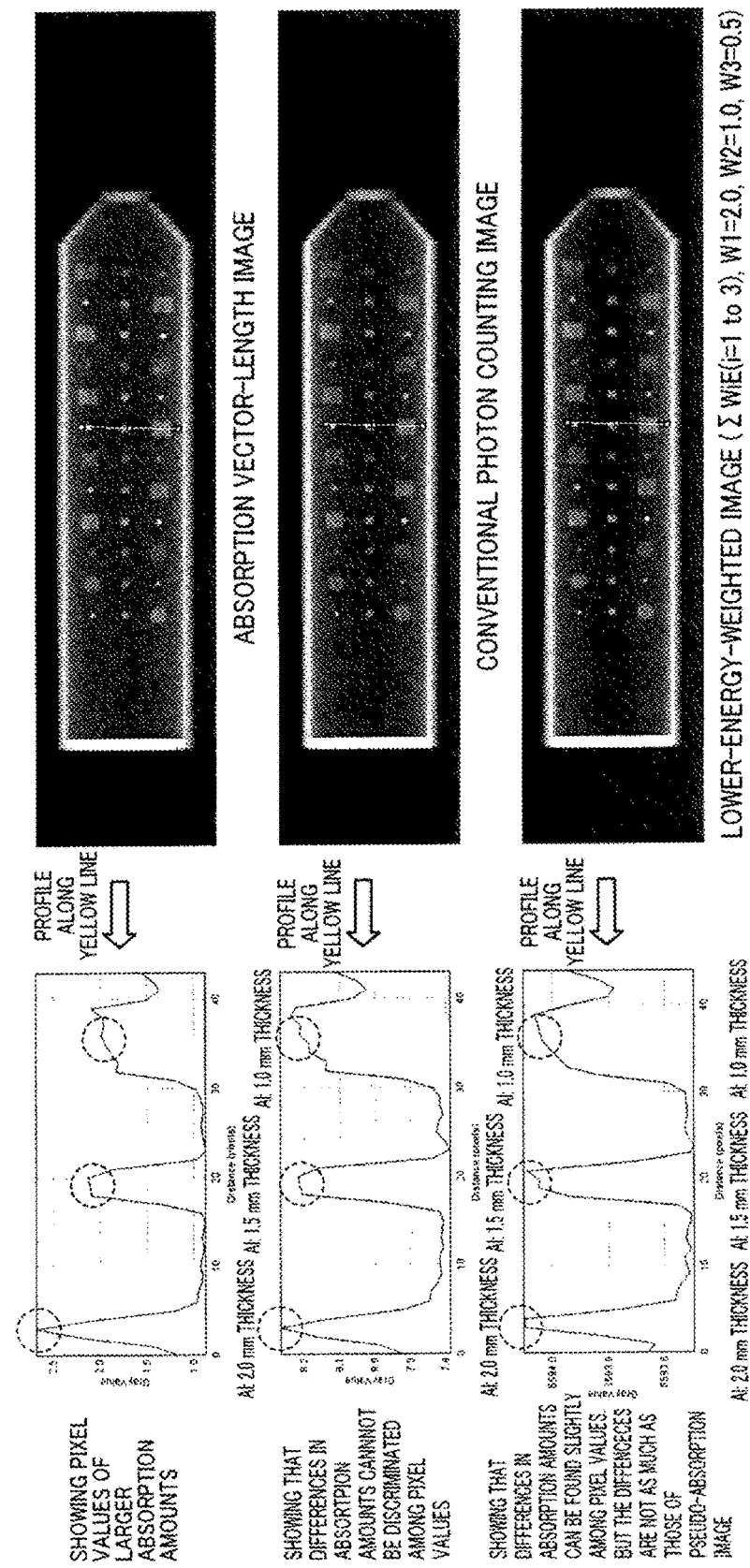
FIG. 15 shows diagrams explaining results of a simulation which uses a phantom in FIG. 14.

FIGS. 14 and 15 show a simulation in relation to the foregoing pseudo absorption image.

As described, the absorption vector-length image can also be produced during a process for producing the three-dimensional scatter diagram. For verifying an advantage of this absorption vector-length image, the inventors conducted a simulation in which the absorption vector-length image (i.e., pseudo absorption image) was compared with two type of images; one is an image produced using laminography technique based on a conventional photon counting (herein referred to as a conventional photon counting image), and the other is an image produced using a laminography based on the photon counts measured in a lower energy range(s) (herein referred to as a lower-energy weighted image).

First a pepper phantom was prepared which is, as shown in FIG. 14, a horizontally long phantom imitating pepper tissue serving as food and which contains three types of metallic foreign matter made of Al, Si and Fe within the phantom. The foreign matter (Al, Si and Fe) consists of, for each of the types (Al, Si and Fe), cylindrical foreign matter whose diameter differs from each other and rectangular-parallelepiped-shaped foreign matter whose dimension differs from each other. These items of foreign matter are arranged, every type thereof, to be located at tomographic planes of 0 cm, 3 cm, 6 cm and 9 cm, respectively, within the phantom along the transverse direction thereof. A scan was performed with this phantom under scanning conditions of a scan speed of 60 m/min, a frame rate of 6600 fps, an air-layer count of 50 counts/pixel, a tube voltage of 50 kV, the first energy range $Bin_1$=15 to 27 keV (effective energy=21.65 keV), the second energy range $Bin_2$=27 to 35 keV (effective energy=31.0 keV), and the third energy range $Bin_3$=35 to 50 keV (effective energy=39.4 keV). An absorption vector-length image, a convectional photon counting image, and a lower-energy weighted image were produced using the laminography technique.

Images of the three types are shown in the right part of FIG. 15. Density profiles obtained at a tomographic plane of 6 cm in each of these three images, that is, at the three Al rectangular parallelepipeds having mutually different dimensions (refer to lines in the right-part images), were calculated. This calculation provides the profiles shown in the left part of FIG. 15. These density profiles show peaks of pixel values (densities) at the Al rectangular parallelepipeds depending on the dimensions thereof. The pseudo absorption image showed the magnitude difference among the peaks (i.e., contrast ratios), so that it is understood that the pseudo absorption image represents pixel values in which absorption amounts are best reflected compared with the other types of images. In other words, it is understood that, compared with the conventional photon counting image and the lower-energy weighted image, the pseudo image is a density image which is able to reflect differences in the X-ray absorption amounts at io higher sensitivity.

As described, the X-ray examination system 11 according to the present embodiment is able to provide the following various operative advantages.

First, a region of interest is set on a tomographic image (which can be referred to as an image) focusing a section (or uneven section) of an object OB being examined, and from this image, background pixel information (background components) which is a background of a substance of interest present in the region of interest is removed. In this case, the interested substance is for example the object itself or foreign matter. Based on this after-removal tomographic image data and X-ray counts at each of the pixels of the region of interest for each of the energy ranges, the inherent transmission feature of the interested substance to the X-rays (for example, the X-ray attenuation coefficients µ) is calculated as the inherent information at each pixel. This inherent information is independent of the magnitude of the thickness t of the substance, thus making it possible to identify or determine the types or properties of substances of interest on the basis of this inherent information. For instance, the calculated inherent information can be compared with known inherent information (i.e., known inherent vector information inherent to the substance: the information has a present allowance range) prepared in advance, so that substance identification can be performed.

In addition, depending on how the region of interest is set, a range of identification of a substance can be adjusted to the whole or a part of an object. In this case, since the inherent information is provided as explained as information inherent to substance type or properties (physical states) which are not affected by the object thickness t, the region of interest can be widened or narrowed appropriately regardless of how the thickness changes positionally. Hence, differently from the conventional substance identification, the substance can be identified more accurately, due to the fact such information is obtained after removal of the background components which are not required for substance identification.

Furthermore, as explained, the vectors composed of the ray attenuation coefficients µ are obtained for each of the energy ranges and normalized for being presented on spherical surface as a three-dimensional scatter diagram. Scattering points (serving as spectrums) show the three-dimensional gradient information (that is, substance-inherent information) of the vectors. Accordingly, only looking at distributions of the scattering points makes it possible to understand that the object OB is made of, for example, metal or not; the object OB contains a different substance (such as foreign matter) or not; and/or how the property of the object OB is (for example, muscle and fat are mixed at what ratio). Such information can be made easier to more visually and quantitatively understand by using the center of gravity of scattering points which tend to fluctuate.

Of course, various observation modes for observing the scatter diagram are provided, which include observation from a position (for example, the origin) located inside the sphere, like the observation of planetariums, or observation of distributions of scattering points with rotating the sphere. Alternatively, besides being a spherical surface, the scatting points can be re-mapped on a planar space in various modes. For example, there can be provided a cone-shaped spherical trigonal pyramid whose apex is located at the coordinate origin and whose base is used for re-mapping. In this case, the scattering points are mapped on intersecting points of the bottom, through which lines extending from the origin pass. Still, the re-mapping can be done using techniques known for projecting a globe onto a plane These re-mapping techniques can be useful when the object and foreign matter which possibly be contained in the object are distinguished from each other.

In addition, in the processing for obtaining the three-dimensional scatter diagram, the absorption vector-length image can also be obtained as above. The present inventors confirmed that this absorption vector-length image is not so dependent on the shapes of energy spectrums of X-rays being radiated, compared with the conventional X-ray absorption image. This confirmation was made using phantoms provided with muscle and fat whose thicknesses are changed little by little. The spectrum shapes include a spectrum shape showing that counts in the central energy region $Bin_2$ are larger than those in both energy ranges adjacent to the central energy region $Bin_2$, as shown in FIG. 2, for example. In the present embodiment, as the process on the formula (8) is performed, differences in the X-ray absorption, which depend on the spectrum shapes, are unlikely to occur, and the counts measured in the lower-energy region in which the ray attention coefficients are the largest are stable.

As a result, this lower dependency on the energy spectrum shape gives this absorption vector-length image various features. These features include a more robust performance to X-ray radiation conditions, such as an X-ray tube voltage, and less noise which is due to the fact that an image contrast is higher and proportional to the ray attenuation values μt and the ray attenuation values μt over all the energy ranges are averaged. Examples in which such advantages are remarkable are as follows.

In medical examinations using an agent of which mass is larger, such as iodine, gadolinium, or gold, beam hardening is caused in portions in which the agent has passed. As a result, the ray attenuation values μt in lower X-ray energy ranges become higher, thereby providing images whose contrast difference is larger between the portion with the passing agent and potions with no passing agent, thus making the effect of the agent greater.

In food foreign matter inspection, a contrast of foreign matter to other areas can be enhanced more than conventionally, thus providing better visual information.

By the way, in the destructive inspection, if there is, as a background, an air portion containing the conveyance belt in the image, the type itself of foreign matter cannot be identified. However it was confirmed that it is possible to detect whether or not there is foreign matter present in an object. That is, the foregoing substance identification approach can also be applied to foreign matter detection. For this detection, the foreign matter detection is first carried out, before examining in detail a portion determined to include the foreign matter. The type of the foreign matter is then identified (i.e., the substance identification to identify the type of a substance). By this two-stage approach, non-destructive inspection is possible.

[Modifications]
<First Modification>

The foregoing substance identification technique is not necessarily limited to be performed in the three-dimensional coordinate system. For example, in the frequency (count) spectrum shown in FIG. 2, two energy ranges $Bin_1$, $Bin_2$; $Bin_2$, $Bin_3$; or $Bin_1$, $Bin_3$ can be used for the foregoing processes such that a two-dimensional scatter diagram and an absorption vector-length image are obtained. This makes it possible to provide both gradients of mass attenuation vector (substance inherent information) which is simplified two-dimensionally, and the lengths (absorbed amounts), which enables substance identification simply in the same way as the above.

<Second Modification>

Additionally, the formula (8) used to calculate the foregoing absorption vector-length image can be generalized as follows.

$$(a\times(\mu_1 t)^2 + b\times(\mu_2 t)^2 + c\times(\mu_3 t)^2)^{1/2} \tag{8'}$$

In this formula, values a, b and c are coefficients which can be any values and used for weighted addition. Absorption vector-length images based on this formula can be used for, for example, designing radiation conditions of the X-ray tube. Designing the radiation condition enables the X-ray tube to radiate X-rays having energy spectrums depending on, for instance, types and specific gravities of substances being examined.

<Third Modification>

Figure 16:
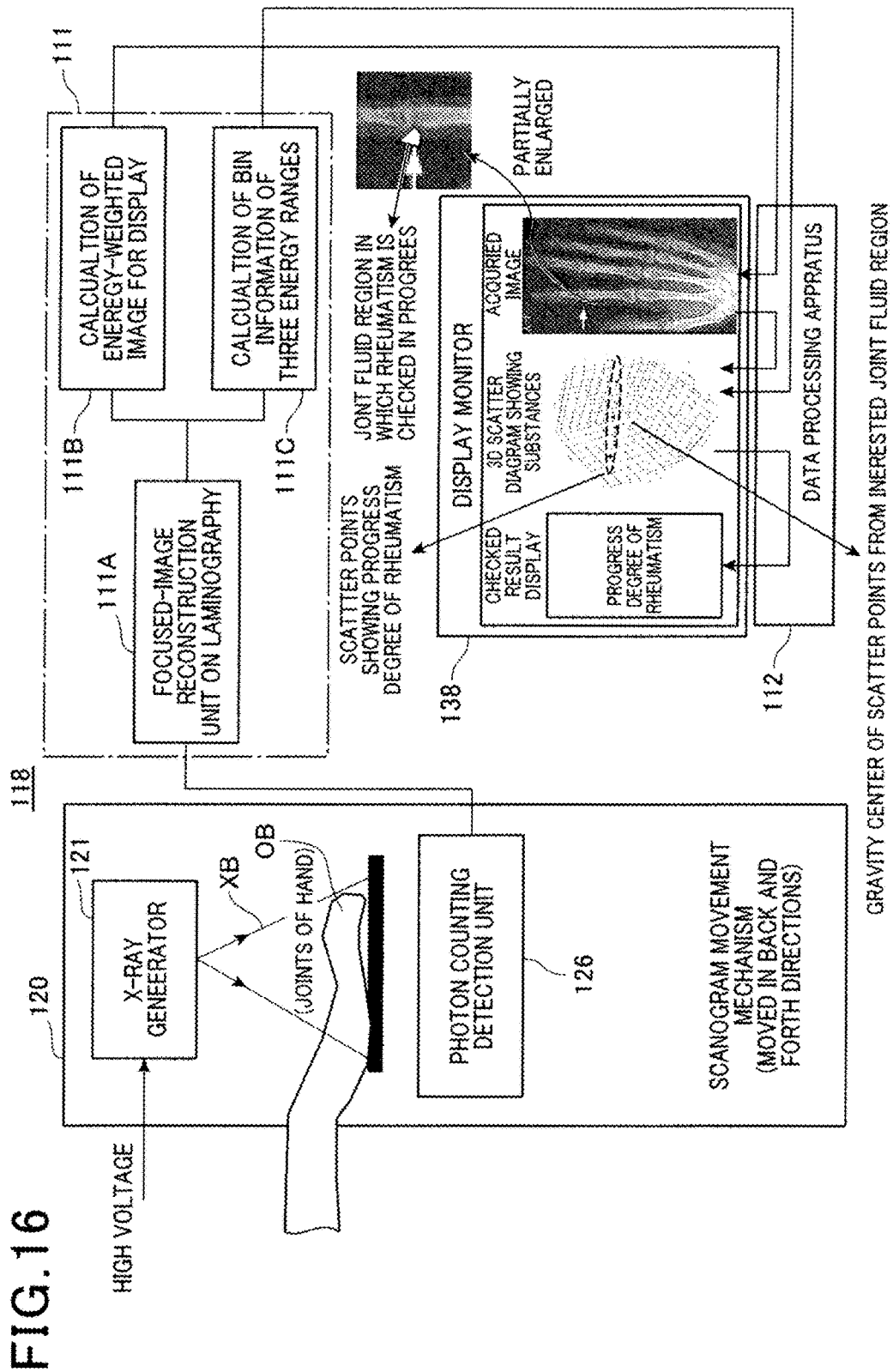
FIG. 16 is a block diagram outlining the configuration of an X-ray examination system exemplified as a medical rheumatism examination apparatus provided with the data processing apparatus (method), which identifies substances, which is explained in the embodiment.

Another modification is shown in FIG. 16, in which the X-ray examination system according to the present invention is provided as a medical rheumatism examination apparatus. As shown, the medical rheumatism examination apparatus 118 is directed to an object OB which is a joint of the hands of a patient. In the apparatus, an X-ray generator 121 and a photon counting detection unit 126 are provided to be opposed to each other with the joint placed therebetween. This pair of units is moved back and forth by a scanogram movement mechanism 120 in a direction perpendicular to the paper in which FIG. 16 is depicted. This rheumatism examination apparatus 118 is equipped with a reconstruction section 111 processing frame data outputted from the detection unit 126, in addition to a data processing apparatus 112 and a display monitor 138. The data processing apparatus 112 performs the process for the foregoing substance identification based on data reconstructed by the reconstruction section 111. The display monitor 138 displays results processed in the processing apparatus 1121.

The reconstruction section 111 is provided with a reconstruction unit 111A, a producing unit 111B, and a processing unit 111C. The reconstruction unit 111A is configured to reconstruct a focused image (an optimally focused image with less blur of the pixels) by applying a laminography approach to the frame data. The producing unit 111B is configured to produce, from the reconstructed focused image, an energy-weighted image for display. The processing unit 111C is configured to perform the foregoing substance identification based on the three energy ranges $Bin_1$, $Bin_2$ and $Bin_3$. Images and information processed by these units 111B and 111C are displayed by the display monitor 138 via the data processing apparatus 112. This data processing apparatus 112 operates to respond to interactive actions with a user such that the images and information are displayed directly on the display monitor 138. By these configurations, images and three-dimensional scatter diagrams produced by the producing unit 111B are presented by the display monitor 138. In addition, the data processing apparatus 112 is configured to be able to perform a process for displaying an enlarged image on the display monitor 138 and a process for displaying, as a lesion medical check, a stage of progression of the rheumatism. These display modes are carried out interactively with the user.

In this way, by applying the foregoing substance identification to the medical check for determining how the joint is in terms of its substance properties (physical states), the rheumatism examination can be carried out at higher accuracies.

Figure 17:
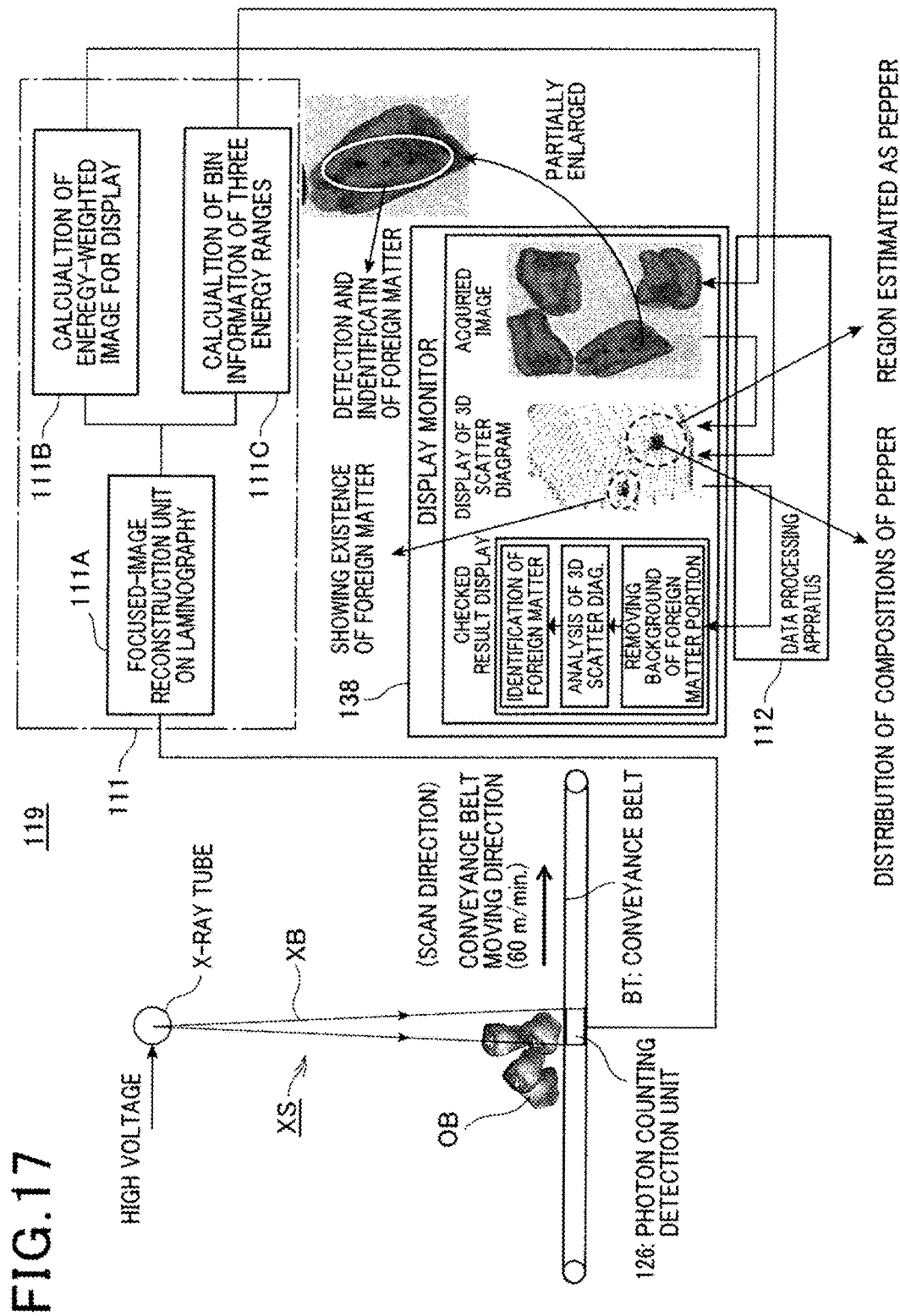
FIG. 17 is a block diagram outlining the configuration of an X-ray examination system exemplified as a nondestructive inspection apparatus provided with the data processing apparatus (method), which identifies substances, which is explained in the embodiment, particularly, the apparatus being an in-line foreign matter inspection apparatus.

Similarly to the above, another modification is shown in FIG. 17, where the X-ray examination system according to the present invention is practiced as a nondestructive inspection apparatus for inspecting foreign matter.

<Fourth Modification>

A nondestructive inspection apparatus 119 is shown in FIG. 17, the apparatus is provided with the reconstruction section 111, the data processing apparatus 112, the display monitor 138, which are described above, and an X-ray scanning mechanism XS. The X-ray scanning mechanism XS employs an arrangement in which the X-ray tube and the photon counting detection unit 126 are located with a conveyance belt BT passing therebetween. Together with movement of the conveyance belt BT, peppers placed on the belt, which are exemplified as objects OB being inspected, move. The movement direction corresponds to a scanning direction along which X-ray beams XB are scanned. Similarly to the previous modification, the reconstruction section 111, the data processing apparatus 112, and the display monitor 138 are provided. The data processing apparatus 112 is capable of displaying various kinds of information about determined results of the substance identification. Such results are foreign matter absent/present information showing whether or not the objects OB contain foreign matter such as metal pieces, and/or, if foreign matter is contained, foreign matter identification information showing the type of the foreign matter or suggesting that type (for example, suggested information is that there is a higher possibility of io containing plastic or metal pieces as foreign matter). Additionally, interactively with a user, the data processing apparatus 112 is configured to produce and display information obtained by analyzing a three-dimensional scatter diagram and/or an image from which a background of foreign matter portion (a portion encircled by the region of interest) is removed.

In this way, the foregoing substance identification can be applied to the foreign matter inspection, whereby the foreign matter can be detected more accurately than conventionally, including checking to determining whether or not foreign matter is present in or on an object being inspected.

It is therefore possible that the technique of identifying a substance, which is according to the present invention, can be applied to various fields.

<Fifth Modification>

In the substance identification process according to the present invention, various other modes of display of the three-dimensional diagram can be provided. Such display modifications are also applicable to the third and fourth modifications, not limited to the application to the foregoing embodiment.

In FIG. 10, the partial spherical surface has been exemplified as the single surface on which points of a three-dimensional scatter diagram are dotted. This surface has the same radius (e.g., a normalized radius of 1). However the surface is not limited to this kind of partial spherical surface, but a whole spherical surface, like a globe, can be used such that scattering points of a three-dimensional scatter diagram are dotted thereon. The dotted points on this whole spherical surface can be observed from the origin inside the sphere or from the outside of the sphere to the origin inside the sphere, and observed pictures can be displayed or presented for users, or can be stored in a memory.

In the present invention, although it is important to dot the scattering points on the same surface, this same surface is not limited to a curved surface having a radius of 1. A planer surface, a part of a sphere or a whole sphere may be used as long as such a surface intersects with the respective axes at points other than 1 of the axes, in which distances from the origin to the points are normalized.

Figure 19:
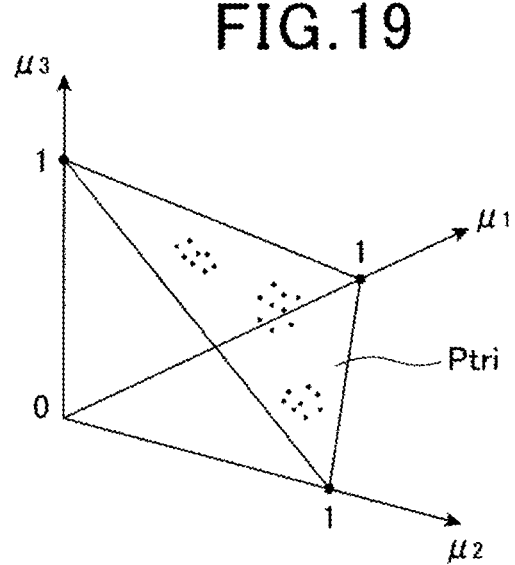
FIG. 19 is a graph explaining a modification concerning display of scattering point data.

Moreover, as a practical example of the same surface, as shown in FIG. 19, a triangular surface (plane) Ptri can be set, where the surface connects a normalized point of 1 in each of the respective three axes indicating pixel vectors ($\mu_1$, $\mu_2$, $\mu_3$). The tip ends of the vectors ($\mu_1$, $\mu_2$, $\mu_3$) stemming from the origin are dotted or mapped on this surface Ptri so as to extend from the origin. A process for this mapping is executed by the data processor 35 in the step S134 in FIG. 7 described. In this example, as a matter of course, a triangular surface may be set to intersect the same points, but not the normalized point of 1,in the three axes.

Figure 20:
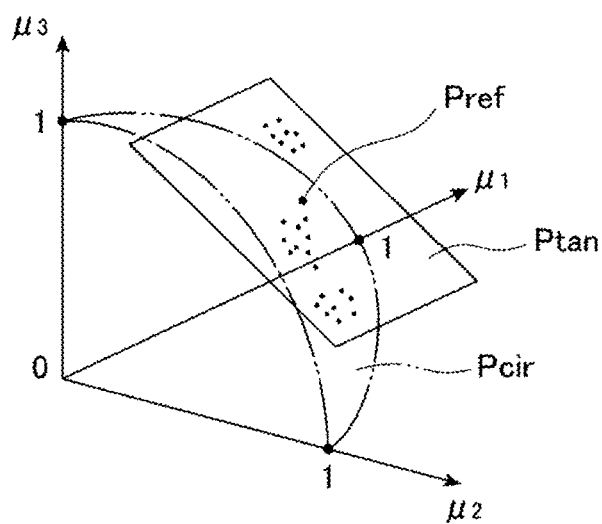
FIG. 20 is a graph explaining another modification concerning display of scattering point data.

Another example is shown in FIG. 20, where a normalized partial spherical surface Pcir shown in FIG. 10 is again provided. In this example, a planar tangent surface Ptan is added, which is tangent to the partial spherical surface Pcir at a reference or desired point (or a representative point) Pref of the scattering points showing a scatter diagram for a substance. And the tip points of vector ($\mu_1$, $\mu_2$, $\mu_3$) are dotted on the planar tangent surface Ptan so as to extend from the coordinate origin O. A process for this mapping can also be executed by the data processor 35 in the step S134 in FIG. 7 described. Similarly to the above, as a matter of course, the tangent surface may be set to be tangent to a point in a partial spherical surface intersecting the same points, but not the normalized point of 1, in the three axes.

Incidentally, in the mapping techniques shown in FIGS. 19 and 20, there occurs distortion in distances among the scattered points on the surface, which is different from that shown in FIG. 10. Hence, the distances can be corrected additionally.

In this way, the scattering points can be mapped on the same surface (i.e., a single surface), so that it is possible to choose the same surface from various and employ various types of design. When employing the planar surface, not the spherical surface, the dotted scattering points, that is, distributions of a three-dimensional scatter diagram can be observed with lesser directivity.

<Sixth Modification>

Figure 21:
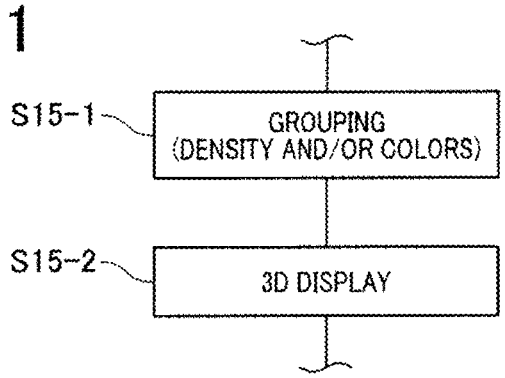
FIG. 21 is a partial flowchart explaining another modification concerning display of scattering point data.

Another modification relates to display of three-dimensional scatter diagrams. When displaying the scatter diagrams on the display unit 38, the data processor 35 is allowed to differentiate from each other, group by group, densities and/or colors (such as hues) of the scattering points. For this display, the data processor 35 can operate as shown in FIG. 21, where, at step S15 described before, densities and/or colors of scattering points being mapped on a spherical surface or part thereof which serves as the same surface are changed (step S15-1), and the grouped scattering points are displayed on the surface which is three-dimensional (step S15-2). This provides various modes of the display.

<Seventh Modification>

Figure 22:
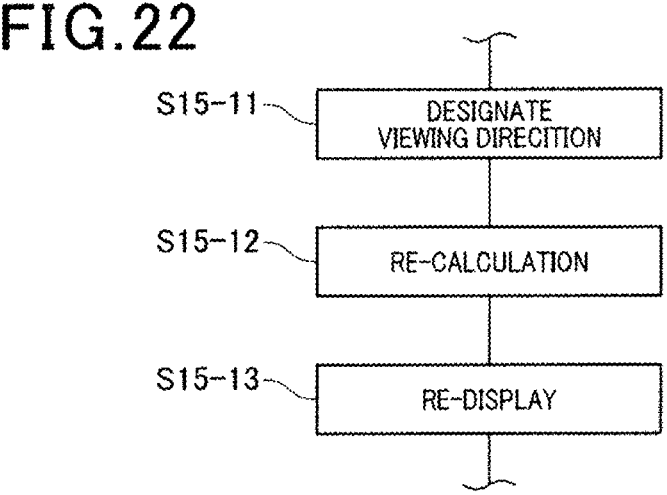
FIG. 22 is a partial flowchart explaining another modification concerning display of scattering point data.
Figure 23:
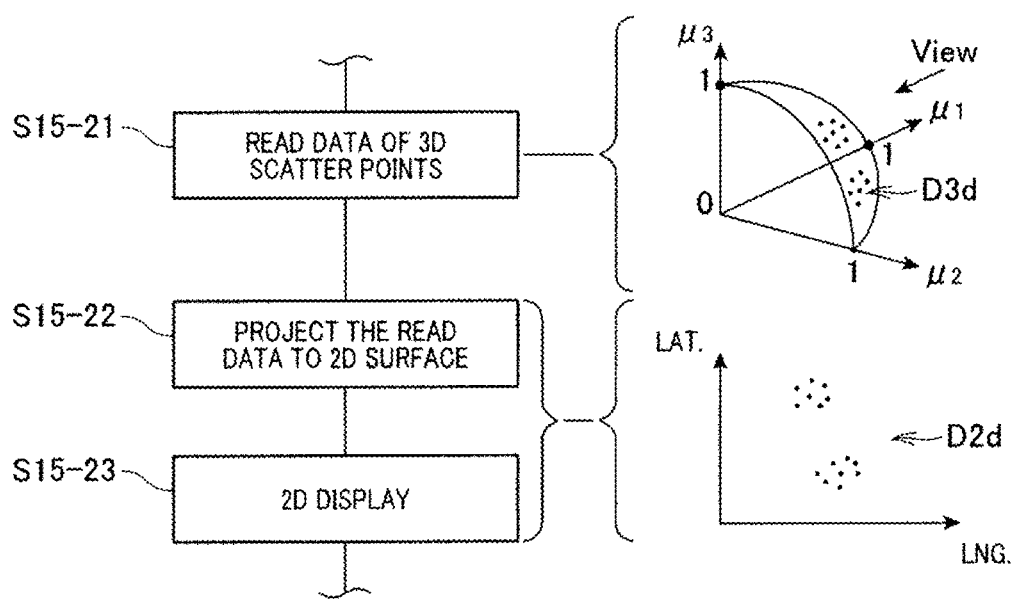
FIG. 23 shows diagrams explaining another modification concerning display of scattering point data.

Another modification relates to changes of a user's line of view along which a user observes a three-dimensional scatter diagram. In this modification, as shown in FIG. 22, the data processor 35 responds to user's interactive commands to designate a line of view along which a user observes, for example, the whole or part of a single special surface from the coordinate origin (step S15-11). This line of view is for example a line along the vector Vobj in FIG. 11(C). Then the data processor 35 re-calculates both the there-dimensional coordinate for the vectors ($\mu_1, \mu_2, \mu_3$) and scattering points to make them rotate so as to be along the designed line of view (step S15-12). Then, the thee-dimensional coordinate and the scattering points are again displayed on the display unit 38 for instance (step S15-13). In response to changes of directions of the line of view, the data processor 35 repeats the processes shown in FIG. 22, resulting rotation and display of the three-dimensional scatter diagram in reply to user's instructions. This is easier for users in handing the diagram and obtaining various display modes.

A variation categorized in the above modification can be provided by the data processor 35 which executes a process at step S15 in a different way. Practically, at step S15, as shown in FIG. 11(C), the three-dimensional scatter diagram is displayed together with the vectors Vobj which have been set. Alternatively, only the spherical surface and the scatting points can be displayed. Only the spherical surface and the centers of gravity, GR, can be displayed. In addition, the spherical surface can be changed to a two-dimensional surface on which scattering points are mapped, so that the two-dimensional surface is displayed with the scattering points.

A further variation can also be accomplished by the data processor 35, if the data processor sets lines of view along the vectors Vobj stemming from the coordinate origin. The data processor then displays both markers indicating the lines of view and the three-dimensional scatter diagram for observation. This makes it possible that when observing and identifying a substance in a micro region on the spherical surface, an observer can observe that region with constant consciousness about a direction toward the coordinate origin, thus almost avoiding the viewing direction from being lost.

As shown by the plural vectors Vobj in FIG. 11(C), the plural lines of view can be set for each of groups GR of the scattering points, and displayed on the display unit 38.

<Eighth Modification>

Another modification also relates to the two-dimensional display of three-dimensionally presented scatting points, which can also be performed by the data processor 35. Practically, the data processor 35 reads three-dimensional scatter diagram data $D_{3d}$ mapped on the whole or part of a spherical surface (FIG. 23, step S15-21), and projects (converts) them into two-dimensional scatter data $D_{2d}$ provided when being observed along a previously designated line of view $V_{iew}$ (step S15-22). For this projection, by way of example, Mercator projection method can be used. The data processor 35 then proceeds to displaying the projected two-dimensional scatter data $D_{2d}$ on the display unit 38 (step S15-23). The user can use two-dimensional images which are used to seeing. Hence, a variety of modes of visual observation can be provided, not limited to the three-dimensional display modes shown in FIGS. 10 and 11.

In the embodiment and modifications thereof described so far, the processes shown in FIGS. 5, 7, 9, and 18-22, which are executed by the data processor 35, there are provided various functional units (which also can be referred to as functional blocks or portions). Practically, steps S1 and S2 in FIG. 5 functionally configure an image calculation unit serving as image calculating means. Step S10 in FIG. 5 functionally configures a region-of-interest setting unit serving as region-of-interest setting means. Steps S11 and S12 in FIG. 5 functionally configure a background removal unit serving as background removing means. Furthermore, step S13 in FIG. 5 (practically steps S131 to S133 shown in FIG. 7) functionally configures an inherent information calculating unit corresponding to inherent information calculating means. Of this means, step S133 functionally configures a normalization unit serving as normalizing means.

Further, the processes at step S134 of FIG. 7 (including steps S134-1 to S134-3 in FIG. 18) and steps S135, which are executed by the data processor 35, functionally configure a scatter diagram producing unit serving as scatter diagram producing means and an image producing unit serving as image producing means, respectively. Step S15 in FIG. 7 functionally produces both a scatter diagram presenting unit serving as scatter diagram presenting means and an image presenting unit serving as image presenting means.

Moreover, the processes at steps S31 to S37 shown in FIG. 9, which are also executed by the data processor 35, functionally configure an analyzing unit serving as analyzing means. Of these steps, step S34 functionally configures a representative point calculating unit serving as representative point calculating means and step S36 functionally comfitures a property determining unit corresponding to property determining means.

Further, the process at step S15-1 of FIG. 21 also executed by the data processor 35 functionally configures a grouping unit serving as grouping means, and the process as step S15-2 functionally configures a three-dimensional displaying unit serving as three-dimensional displaying means. Similarly, in FIG. 22, step S15-11 functionally corresponds to a line-of-view designating unit serving as line-of-view designating means, step S15-12 functionally corresponds to a re-calculating unit serving as re-calculating means, and step S15-13 functionally corresponds to a re-displaying unit serving as re-displaying means. Still similarly, the processes at steps S15-21 and S15-22 in FIG. 23 functionally configure a projecting unit serving as projecting means, while the process at step S15-23 functionally configures a two-dimensional displaying unit serving as two-dimensional displaying means.

The various modes of the data processing apparatus, the data processing method, and the X-ray examination system according to the present invention have been described, but the present invention is not limited to the features disclosed by such modes. It is therefore possible to change the modes without departing from gist of the present invention.

REFERENCE SIGNS LIST

10 X-ray examination system (X-ray examination system provided with data processing apparatus: X-ray examination system capable of performing data processing method)
12 computer system (data processing apparatus)
21 X-ray tube
24 detector
25 data acquisition circuit
26 detection unit
12 data processing apparatus
32 buffer memory (memorization means)
33 ROM
34 RAM
35 data processor
36 image memory (memorization means)
37 input unit
38 display unit
111 reconstruction section
112 data processing apparatus
118 X-ray examination system serving as medical rheumatism examination apparatus
119 X-ray examination system serving as nondestructive inspection apparatus for detecting foreign matter
138 display unit
OB object being examined (object)

The invention claimed is:

1. A data processing apparatus processing counts detected at each of pixels of a photon counting detector in each of a plurality of energy ranges of X-rays, the X-rays being radiated from an X-ray tube, transmitted through an object, comprising:
   image calculating means for calculating an image of the object based on the counts;
   region-of-interest setting means for setting a region of interest on the image;
   background removing means for removing, from the image, pixel information showing a background present in the region of interest;
inherent information calculating means for calculating, pixel by pixel,
   i) as inherent information inherent to a substance of the object, scatter diagram information showing a transmission characteristic of the X-rays at the respective pixels as mass attenuation vectors in the respective energy ranges, based on the counts detected at each of the respective pixels in every one of the energy ranges of the X-rays in the region of interest, the inherent information indicating, the transmission characteristic inherent to the X-rays provided when the X-rays are transmitted through the substance, and
   ii) attenuation information showing both lengths of the mass attenuation vectors and an attenuated degree of the X-rays attenuated due to the substance based on the mass attenuation vectors;
   image producing means for producing a two-dimensional absorption vector-length image whose pixels are presented by the attenuation information; and
   image presenting means for presenting, on a display as a two-dimensional image, the absorption vector-length image.

2. The data processing apparatus of claim 1, wherein
the inherent information calculating means comprises
   scatter diagram producing means for producing, as a scatter diagram, scattering point data of two or more dimensions from the scatter diagram information; and
the image presenting means comprises
   scatter diagram presenting means for presenting the scatter diagram.

3. The data processing apparatus of claim 2, wherein the two or more dimensions are either a three dimension or a two dimension.

4. The data processing apparatus of claim 2, wherein
the space of the dimension is a three dimensional space;
the inherent information calculating means calculate, at each of the pixels, as the inherent information, a three-dimensional vector whose start point is an origin of a three-dimensional space, and
the scatter diagram producing means produce the scattering point data in the three-dimensional space.

5. The data processing apparatus of claim 4, wherein
the inherent information calculating means comprises
   normalizing means for normalizing the three-dimensional vectors, pixel by pixel.

6. The data processing apparatus of claim 4, wherein
the scatter diagram producing means produce, as the scattering point data, data showing directions of the three-dimensional vectors having start points and end points, the start points being located at the origin of the three-dimensional space, the end points being mapped on a single surface.

7. The data processing apparatus of claim 6, wherein the single surface is either whole or a part of a sphere, the sphere having a radius from the origin, the radius being constant.

8. The data processing apparatus of claim 7, comprising
   projecting means for two-dimensionally projecting a whole or a part of the surface of the sphere, the scattering points being displayed on the surface; and
   two-dimensional displaying means for displaying the whole or the part of the two-dimensional surface projected by the projecting means.

9. The data processing apparatus of claim 6, wherein the single surface is a planar surface which intersects with points in respective axes defining the three-dimensional space, the intersecting points being equal to each other in distances from the origin.

10. The data processing apparatus of claim 6,
further comprising an analyzing means for analyzing a property of the substance by analyzing the scattering point data to identify a type of the substance, to identify a state of the substance, or to detect either another substance different from the substance or a specified substance.

11. The data processing apparatus of claim 10, wherein
the analyzing means comprises
   representative point calculating means for grouping a plurality of the scattering points mapped on the single surface and calculating, as a representative point, a center of gravity in each group of the scatting points; and
   property determining means for determining a property of the substance which is present within the region of interest and a property of another substance which is present around the substance within the region of interest, by comparing positional information with a previously stored reference positional information.

12. The data processing apparatus of claim 11, wherein the scatter diagram presenting means comprise grouping means for changing, group by group in the groups of the scattering points, at least one of densities and colors of the scattering points for display; and three-dimensional displaying means for three-dimensionally displaying the grouped scattering points on the single surface.

13. The data processing apparatus of claim 12, comprising line of view designating means for designating a line of view when the single surface is observed, the scattering points being displayed on the single surface by the three-dimensional displaying means;
re-calculating means for re-calculating positions of the scattering points being mapped on the single surface in a three-dimensional coordinate rotated according to the line of view designated by the line of view designating means; and
re-displaying means for re-displaying both the three-dimensional coordinate and the scattering points on the single surface, which are re-calculated by the re-calculating means.

14. The data processing apparatus of claim 10, wherein the analyzing means is configured to identify the type of the substance which is present within the region of interest.

15. The data processing apparatus of claim 10, wherein the analyzing means is configured to identify the property of the substance which is present within the region of interest.

16. The data processing apparatus of claim 10, wherein the analyzing means is configured to detect that there is a substance different from the object itself in the region of interest or to identify the type of the substance different from the object itself.

17. A data processing apparatus processing counts detected at each of pixels of a photon counting detector in each of a plurality of energy ranges of X-rays, the X-rays being radiated from an X-ray tube, transmitted through an object, comprising:
a non-transitory computer readable medium in which a computer readable program is stored in advance;
a processor provided with a CPU executing sequentially procedures given by the program read from the non-transitory computer readable medium; and
an interface obtaining information from outside the data processing apparatus,
wherein the procedures enable the processor to
calculate an image of the object based on the counts in response to the information obtained through the interface, under execution of the procedures of the CPU,
set a region of interest on the image,
remove, from the image, pixel information showing a background present in the region of interest,
calculate, pixel by pixel, i) as inherent information inherent to a substance of the object, scatter diagram information showing a transmission characteristic of the X-rays at the respective pixels as mass attenuation vectors in the respective energy ranges, based on the counts detected at each of the respective pixels in every one of the energy ranges of the X-rays in the region of interest, the inherent information indicating, the transmission characteristic inherent to the X-rays provided when the X-rays are transmitted through the substance, and ii) attenuation information showing both lengths of the mass attenuation vectors and an attenuated degree of the X-rays attenuated due to the substance based on the mass attenuation vectors;
produce a two-dimensional absorption vector-length image whose pixels are presented by the attenuation information; and
present on a display, as a two-dimensional image, the absorption vector-length image.

18. An X-ray examination system, comprising
an X-ray source radiating X-rays;
a photon counting X-ray detector;
a data processing apparatus, the processing apparatus processing counts detected at each of pixels of the photon counting detector in each of a plurality of energy ranges of X-rays, the X-rays being radiated from the X-ray source, transmitted through an object; and
wherein the data processing apparatus comprises:
image calculating means for calculating an image of the object based on the counts;
region-of-interest setting means for setting a region of interest on the image;
background removing means for removing, from the image, pixel information showing a background present in the region of interest;
inherent information calculating means for calculating, pixel by pixel, i) as inherent information inherent to a substance of the object, scatter diagram information showing a transmission characteristic of the X-rays at the respective pixels as mass attenuation vectors in the respective energy ranges, based on the counts detected at each of the respective pixels in every one of the energy ranges of the X-rays in the region of interest, the inherent information indicating, the transmission characteristic inherent to the X-rays provided when the X-rays are transmitted through the substance, and
ii) attenuation information showing both lengths of the mass attenuation vectors and an attenuated degree of the X-rays attenuated due to the substance based on the mass attenuation vectors;
image producing means for producing a two-dimensional absorption vector-length image whose pixels are presented by the attenuation information; and
image presenting means for presenting on a display, as a two-dimensional image, the absorption vector-length image.

19. A data processing method processing counts detected at each of pixels of a photon counting detector in each of a plurality of energy ranges of X-rays, the X-rays being radiated from an X-ray tube, transmitted through an object, the method comprising steps of:
calculating an image of the object based on the counts;
setting a region of interest on the image;
removing, from the image, pixel information showing a background present in the region of interest; and
calculating, pixel by pixel, i) as inherent information inherent to a substance of the object, scatter diagram information showing a transmission characteristic of the X-rays at the respective pixels as mass attenuation vectors in the respective energy ranges, based on the counts detected at each of the respective pixels in every one of the enemy ranges of the X-rays in the region of interest, the inherent information indicating, the transmission characteristic inherent to the X-rays provided when the X-rays are transmitted through the substance, and ii) attenuation information showing both lengths of the mass attenuation vectors and an attenuated degree of the X-rays attenuated due to the substance based on the mass attenuation vectors;

producing a two-dimensional absorption vector-length image whose pixels are presented by the attenuation information; and presenting, as a two-dimensional image, the absorption vector-length image.

* * * * *